(12) United States Patent
Sugawara et al.

(10) Patent No.: US 10,851,475 B2
(45) Date of Patent: Dec. 1, 2020

(54) ELECTROSPINNING APPARATUS AND SYSTEMS AND METHODS THEREOF

(71) Applicant: Kao Corporation, Tokyo (JP)

(72) Inventors: Hirokatsu Sugawara, Cincinnati, OH (US); Shinji Kodama, Inage-ku (JP); Michael Edward Philip Russell, Cambridgeshire (GB); Carl Gordon Hewett, Cambridgeshire (GB); Joe Antony Williams, Haverhill (GB)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 16/195,287

(22) Filed: Nov. 19, 2018

(65) Prior Publication Data

US 2019/0153623 A1 May 23, 2019

Related U.S. Application Data

(60) Provisional application No. 62/589,173, filed on Nov. 21, 2017.

(51) Int. Cl.
*B05B 5/025* (2006.01)
*B05B 5/16* (2006.01)
(Continued)

(52) U.S. Cl.
CPC ........... *D01D 5/0061* (2013.01); *A45D 34/00* (2013.01); *A45D 34/04* (2013.01); *A45D 40/00* (2013.01);
(Continued)

(58) Field of Classification Search
CPC .... B05B 5/1691; B05B 5/025; D01D 5/0061; A45D 40/00; A45D 34/00; A61K 8/046; A61M 35/003
See application file for complete search history.

(56) References Cited

U.S. PATENT DOCUMENTS 4,549,243 A * 10/1985 Owen .................... B05B 5/0255
239/690
6,311,903 B1 11/2001 Gaw et al.
(Continued)

FOREIGN PATENT DOCUMENTS

| CN | 1379701 A | 11/2002 |
|----|-----------|---------|
| WO | WO 2014/118584 A1 | 8/2014 |
| WO | WO 2017/082179 A1 | 5/2017 |

OTHER PUBLICATIONS

International Search Report dated Feb. 25, 2019 in PCT/US 18/61840, 2 pages.
(Continued)

*Primary Examiner* — Binu Thomas
(74) *Attorney, Agent, or Firm* — Oblon, McClelland, Maier & Neustadt, L.L.P.

(57) ABSTRACT

A portable, hand-held electrospinning or electrospraying apparatus and system, method, and portions thereof, comprised of a durable portion of the hand-held apparatus and a consumable portion of the hand-held apparatus. The consumable portion of the hand-held apparatus, which may contain the solution to be output in electrospin or electrospray fashion, may be replaced in whole or in part to provide additional or alternative solution. A base station may be provided, and can output high voltage and communication signals to the hand-held apparatus to enable the electrospin or electrospray operation by the hand-held apparatus.

19 Claims, 8 Drawing Sheets

(51) Int. Cl.
<table>
<tr><td>B05B 5/053</td><td>(2006.01)</td></tr>
<tr><td>D01D 5/00</td><td>(2006.01)</td></tr>
<tr><td>B05B 12/00</td><td>(2018.01)</td></tr>
<tr><td>B05B 11/00</td><td>(2006.01)</td></tr>
<tr><td>D01D 13/00</td><td>(2006.01)</td></tr>
<tr><td>A45D 34/04</td><td>(2006.01)</td></tr>
<tr><td>A45D 40/00</td><td>(2006.01)</td></tr>
<tr><td>A45D 40/26</td><td>(2006.01)</td></tr>
<tr><td>A45D 34/00</td><td>(2006.01)</td></tr>
<tr><td>A61K 8/04</td><td>(2006.01)</td></tr>
<tr><td>B05B 12/12</td><td>(2006.01)</td></tr>
<tr><td>A61M 35/00</td><td>(2006.01)</td></tr>
<tr><td>A61M 15/02</td><td>(2006.01)</td></tr>
</table>

(52) U.S. Cl.
CPC .............. *A45D 40/26* (2013.01); *A61K 8/046* (2013.01); *B05B 5/025* (2013.01); *B05B 5/0538* (2013.01); *B05B 5/1691* (2013.01); *B05B 11/00* (2013.01); *B05B 12/004* (2013.01); *D01D 5/003* (2013.01); *D01D 5/0069* (2013.01); *D01D 13/00* (2013.01); *A61M 15/02* (2013.01); *A61M 35/003* (2013.01); *B05B 12/124* (2013.01)

(56) References Cited

U.S. PATENT DOCUMENTS

| | | | | |
|---|---|---|---|---|
| 6,318,647 | B1* | 11/2001 | Gaw | B05B 5/1691 |
| | | | | 239/690 |
| 6,595,208 | B1* | 7/2003 | Coffee | B05B 5/0255 |
| | | | | 239/690 |
| 6,753,454 | B1* | 6/2004 | Smith | D01D 5/0076 |
| | | | | 602/41 |
| 7,960,711 | B1 | 6/2011 | Sheehan et al. | |
| 2001/0020652 | A1 | 9/2001 | Kadlubowski et al. | |
| 2001/0020653 | A1 | 9/2001 | Wilson et al. | |
| 2001/0023902 | A1 | 9/2001 | Wilson et al. | |
| 2001/0038047 | A1 | 11/2001 | Wilson et al. | |
| 2004/0021017 | A1* | 2/2004 | Sumiyoshi | B05B 5/1691 |
| | | | | 239/690 |
| 2006/0180143 | A1* | 8/2006 | Lind | B05B 5/0255 |
| | | | | 128/200.14 |
| 2017/0239094 | A1* | 8/2017 | Dubson | D01D 5/0061 |
| 2018/0317627 | A1 | 11/2018 | Fukuda et al. | |

OTHER PUBLICATIONS

Written Opinion of the International Searching Authority dated Feb. 25, 2019 in PCT/US 18/61840, 15 pages.

\* cited by examiner

ELECTROSPINNING APPARATUS AND SYSTEMS AND METHODS THEREOF

CROSS REFERENCE TO RELATED APPLICATION

This application claims the benefit and priority of U.S. Provisional Patent Application No. 62/589,173, filed Nov. 21, 2017, the entire content and disclosure of which is incorporated by reference into the present application.

FIELD

Embodiments of the disclosed subject matter are directed generally to electrospinning apparatuses and systems and methods thereof. More particularly, embodiments of the disclosed subject matter are directed to portable, hand-held electrospinning apparatuses and systems, methods, and portions thereof.

SUMMARY

According to one or more embodiments of the present disclosure, a portable, hand-held electrospinning or electrospraying apparatus may be provided. The hand-held apparatus may be comprised of a durable portion and a consumable portion. The consumable portion of the hand-held apparatus, which may contain the solution to be output in electrospin or electrospray fashion, may be replaced in whole or in part to provide additional or alternative solution. A base station may also be provided, and can output high voltage and communication signals to the hand-held apparatus to enable the electrospin or electrospray operation by the hand-held apparatus.

Also, in one or more embodiments, a portable, hand-held device for electrospinning or electrospraying toward a deposit surface a predetermined solution formulated for the device is provided. The device can comprise: a durable portion; and a consumable portion coupled to the durable portion. The consumable portion can include: a hollow nozzle configured to output the solution from a nozzle tip thereof, the hollow nozzle having a hollow electrode that defines a first portion of a flow path of the solution to outside the device, and the nozzle tip defines a second portion of the flow path, and a housing configured to contain a predetermined maximum volume of the solution, and output the solution to the hollow electrode. The durable portion can include: a drive mechanism configured to cause solution from the housing to be output to the hollow electrode, and a user control interface configured to receive manual input from a user to control the drive mechanism and application of a high voltage to the hollow electrode to create an electric field for application to the solution to electrospin or electrospray the solution from the hollow nozzle toward the deposit surface. Circuitry can be configured to provide the high voltage to the hollow electrode.

Embodiments also include a portable, hand-held device for electrospinning toward a deposit surface a predetermined solution formulated for the device. The device can comprise: a durable portion; and a consumable portion coupled to the durable portion. The consumable portion can include: a hollow nozzle configured to output the solution from a nozzle tip thereof, the hollow nozzle having a hollow electrode that defines a first portion of a flow path of the solution to outside the device, and the nozzle tip defines a second portion of the flow path, the hollow electrode being configured to output received high voltage supplied via a first conduction path, another electrode configured to output a received high voltage supplied via a second conduction path different from the first conduction path, and a housing configured to contain a predetermined maximum volume of the solution, and output the solution to the hollow electrode. The durable portion can include a drive mechanism configured to cause solution from the housing to be output to the hollow electrode, and a user control interface configured to receive manual input from a user to control the drive mechanism and application of the high voltage to the hollow electrode and the high voltage to the another electrode to create an electric field for application to the solution to electrospin the solution from the hollow nozzle toward the deposit surface. Circuitry can be configured to provide the high voltage to the hollow electrode and the another electrode.

According to one or more embodiments, an electrospinning or electrospraying system can comprise: means for providing high voltage; means for generating an electric field and applying the electric field to solution based on the high voltage; means for outputting the solution to receive application of the electric field; means for outputting the solution as electrospun or electrosprayed solution; and means for controlling the means for generating the electric field and the means for outputting the solution as the electrospun or electrosprayed solution.

Embodiments can also include methods of providing, making, and/or using devices and systems according to embodiments of the disclosed subject matter.

BRIEF DESCRIPTION OF THE DRAWINGS

The accompanying drawings, which are incorporated in and constitute a part of the specification, are illustrative of one or more embodiments of the disclosed subject matter, and, together with the description, explain various embodiments of the disclosed subject matter. Further, the accompanying drawings have not necessarily been drawn to scale, and any values or dimensions in the accompanying drawings are for illustration purposes only and may or may not represent actual or preferred values or dimensions. Where applicable, some or all select features may not be illustrated to assist in the description and understanding of underlying features.

DETAILED DESCRIPTION

Figure 1:
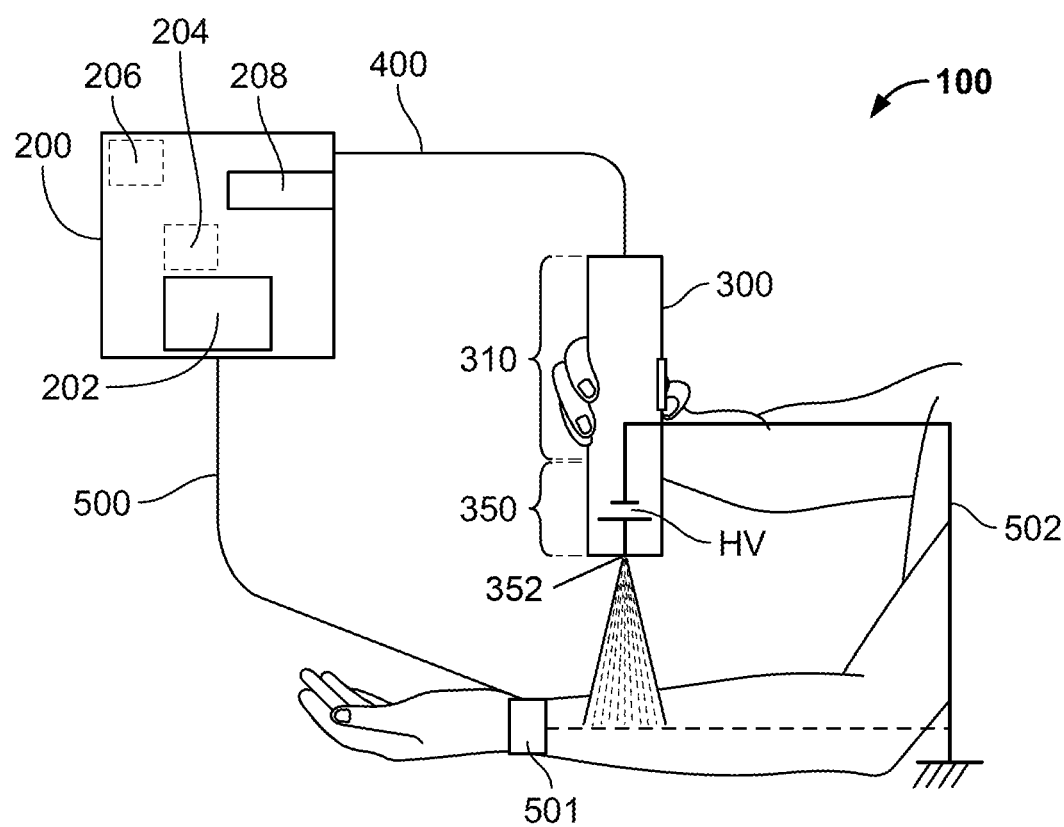
FIG. 1 is a diagram of a system according to one or more embodiments of the disclosed subject matter.

The description set forth below in connection with the appended drawings is intended as a description of various embodiments of the described subject matter and is not necessarily intended to represent the only embodiment(s). In certain instances, the description includes specific details for the purpose of providing an understanding of the described subject matter. However, it will be apparent to those skilled in the art that embodiments may be practiced without these specific details. In some instances, structures and components may be shown in block diagram form in order to avoid obscuring the concepts of the described subject matter. Wherever possible, the same reference numbers will be used throughout the drawings to refer to the same or the like parts.

Any reference in the specification to "one embodiment" or "an embodiment" means that a particular feature, structure, characteristic, operation, or function described in connection with an embodiment is included in at least one embodiment. Thus, any appearance of the phrases "in one embodiment" or "in an embodiment" in the specification is not necessarily referring to the same embodiment. Further, the particular features, structures, characteristics, operations, or functions may be combined in any suitable manner in one or more embodiments, and it is intended that embodiments of the described subject matter can and do cover modifications and variations of the described embodiments.

It must also be noted that, as used in the specification, appended claims and abstract, the singular forms "a," "an," and "the" include plural referents unless the context clearly dictates otherwise. That is, unless clearly specified otherwise, as used herein the words "a" and "an" and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein, merely describe points of reference and do not necessarily limit embodiments of the described subject matter to any particular orientation or configuration. Furthermore, terms such as "first," "second," "third," etc. merely identify one of a number of portions, components, points of reference, operations and/or functions as described herein, and likewise do not necessarily limit embodiments of the described subject matter to any particular configuration or orientation.

Embodiments of the disclosed subject matter are directed generally to electrospinning apparatuses and systems and methods thereof. More particularly, embodiments of the disclosed subject matter are directed to portable, hand-held electrospinning apparatuses and systems, methods, and portions thereof. Embodiments of the disclosed subject matter may also involve, or may be directed to, portable, hand-held electrospraying apparatuses and systems, methods, and portions thereof. In that embodiments of the disclosed subject matter can involve portable, hand-held electrospinning or electrospraying apparatuses and systems, methods, and portions thereof, such embodiments may be used in a clinical, salon, or at-home setting.

Generally speaking, electrospinning, which may be referred to as electric-field spinning, involves generating an electric field (EF) in and around a solution, for instance, a polymer solution, to draw out the solution to create relatively a fine fiber. The high voltage must be sufficiently high to generate an electric field sufficient to produce a Taylor cone. A plurality of such fibers may form a mesh or web on a surface, such as skin, for instance.

The fiber diameter may be as small as a nanometer, for instance. That is, when the deposit of fibers is formed with the electrostatic spraying method, the thickness of the fibers expressed as a diameter of a corresponding circle can be preferably 10 nm or more, and more preferably 50 nm or more. In addition, the thickness can be preferably 3,000 nm or less, and more preferably 1,000 nm or less. The thickness of the fibers can be measured by observing the fibers magnified 10,000 times using a scanning electron microscopy (SEM), for example, removing defects (mass of fibers, intersection of fibers, and droplets) from the two-dimensional images of the fibers, selecting any ten fibers, drawing a line orthogonal to the longitudinal direction of each of the fibers, and reading the diameter of the fiber directly.

Preferable, in one or more embodiments, the fiber is continuous fiber. The fiber can be a continuous fiber having an infinite length in the formation; it is preferable that the fiber has a length at least 100 times longer than its thickness. In this specification, a fiber having a length over 100 times than its thickness is defined as a "continuous fiber." It is preferable that a coating formed with the electrostatic spraying method is a porous discontinuous coating including the deposit of continuous fibers.

Alternatively, one or more embodiments of the disclosed subject matter may involve electrospraying, which, generally, may involve generating an electric field (EF) relative to a solution, for instance, a polymer solution, to output droplets of the solution.

The flow rate of the output solution (F) may be about 0.17 ml/min, preferably about 0.07 ml/min, more preferably about 0.01 to about 0.50 ml/min, even more preferable about 0.0.03 to about 0.40 ml/min, and most preferably about 0.05 to about 0.3 ml/min. Further, the flow rate may be caused or set based on current and voltage supplied to create the electric field, and desired fiber or droplet properties to be output. The flow rate may also be dependent upon characteristics of the solution, such as molecular weight, type, conductivity; environmental aspects, such as ambient temperature and/or ambient humidity; and apparatus configuration, such as the configuration of the nozzle.

The voltage supplied to create the electric field (V) is preferably from about 8 kV to about 30 kV, more preferably from about 9 kV to about 25 kV, and even more preferably from about 10 kV to about 20 kV.

The relational expression of the voltage (V) and the flow rate (F) may be preferably (F)=0.015*(V)+0.1, more preferable (F)=0.012*(V)+0.12, and even more preferable (F)=0.08*(V)+0.15. Set forth below are non-limiting examples of flow rate according to one or more embodiments of the disclosed subject matter.

flow rate (F) 0.01~0.5 mL/min←(V)voltage 8~30 kV
$F=0.015*V+0.1$.

flow rate (F) 0.03~0.4 mL/min←voltage 9~25 kV
$F=0.012*V+0.12$.

flow rate (F) 0.05~0.3 mL/min←voltage 10~20 kV
$F=0.08*V+0.15$.

The solution can have a viscosity of preferably about 1 mPa·s to about 1,200 mPa·s, more preferably about 50 mPa·s to about 500 mPa·s, most preferably about 100 mPa·s to about 300 mPa·s. The viscosity can be measured according to one or more viscometer methodologies or types, such as a spindle-type (B-type) viscometer or a cone-plate-type (E-type) viscometer. For example, the spindle-type viscosity measurement can be performed using a type B viscometer (e.g., TVB-10 by TOKI SANGYO Co. LTD.) under the following characteristics/conditions: spindle No. M2 (21); rotational speed 60 rpm; and temperature 25° C. Additionally or alternatively, the cone-plate-type viscosity measurement can be performed using a type E viscometer (e.g., VISCON EMD by TOKYO KEIKI INC.) under the following characteristics/conditions: cone-plate rotor no. 43; rotational speed selected according to the specification of the viscometer according to the viscosity level: speed of 1 rpm:more than 1280 mPa·s, 10 rpm:more than 128 and less than 1280 mPa·s, and 100 rpm:less than 128 mPa·s; and temperature 25° C.

As noted above, the solution may be a polymer solution, in one or more embodiments of the disclosed subject matter. For example, the polymer solution may preferably be a water insoluble polymer having a coating formation ability, for instance, including completely saponified polyvinyl alcohol, which can be insolubilized after the formation of a coating; partially saponified polyvinyl alcohol, which can be cross-linked after the formation of a coating when used in combination with a cross-linking agent; oxazoline modified silicone such as a poly(N-propanoylethyleneimine)-grafted dimethylsiloxane/γ-aminopropylmethylsiloxane copolymer; polyvinylacetal diethylamino acetate; zein (main component of corn proteins); polyester; polylactic acid (PLA); an acrylic resin such as a polyacrylonitrile resin or a polymethacrylic acid resin; a polystyrene resin; a polyvinyl butyral resin; a polyethylene terephthalate resin; a polybutylene terephthalate resin; a polyurethane resin; a polyamide resin; a polyimide resin; and a polyamideimide resin. More preferably the polymer solution can be or comprise polyvinyl butyral resin. The term "water-insoluble polymer" as used herein can refer to a polymer having a property such that when 1 g of the polymer is weighed out and immersed in 10 g of ion-exchanged water in an environment at a pressure of 1 atmosphere and a temperature of 23° C. for 24 hours, more than 0.5 g of the immersed polymer does not dissolve in the water. Optionally, the polymer solution can preferably lack suspended solids (e.g., powder). That is, the polymer solution may be free or substantially free of suspended solids (e.g., powder).

Additionally or alternatively, in one or more embodiments of the disclosed subject matter, the solution may be a liquid agent comprising component (a), component (b), and component (c) as follows: component (a) may be one or more volatile substances selected from the group consisting of alcohols and ketones; component (b) may be water; and component (c) may be one or more polymers having a coating formation ability.

Preferable examples of alcohols that may serve as the volatile substance to be used as the component (a) include chain aliphatic monohydric alcohols, cyclic aliphatic monohydric alcohols, and aromatic monohydric alcohols. Specific examples thereof include ethanol, isopropyl alcohol, butyl alcohol, phenylethyl alcohol, propanol, and pentanol. One or more alcohols selected from these alcohols can be used. Examples of ketones serving as the volatile substance to be used as the component (a) can include acetone, methyl ethyl ketone, and methyl isobutyl ketone. These ketones can be used alone or in combination of two or more. The volatile substance to be used as the component (a) can be more preferably at least one member selected from ethanol, isopropyl alcohol, and butyl alcohol, even more preferably at least one member selected from ethanol and butyl alcohol, and even more preferably ethanol. Optionally, the solution can contain greater than 70% alcohol.

Generally speaking, component (a) can be volatile and disperse or dissolve component (c). The term "disperse or dissolve" as used herein can refer to a state in which a substance is in a dispersed state at 20° C. and the dispersion is uniform when visually observed, and preferably transparent or translucent when visually observed.

Component (c) can be preferably hydrophobicity (water-insoluble). For example, in the case of the polymer having a coating formation ability, a polymer can be used that is appropriate according to the properties of the volatile substance to be used as the component (a). Specifically, polymers having a coating formation ability may be roughly classified into water-soluble polymers and water-insoluble polymers. The term "water-soluble polymer" as used herein can refer to a polymer having a property such that when 1 g of the polymer is weighed out and immersed in 10 g of ion-exchanged water in an environment at a pressure of 1 atmosphere and a temperature of 23° C. for 24 hours, 0.5 g or more of the immersed polymer dissolves in the water. On the other hand, as noted above, the term "water-insoluble polymer" as used herein can refer to a polymer having a property such that when 1 g of the polymer is weighed out and immersed in 10 g of ion-exchanged water in an environment at a pressure of 1 atmosphere and a temperature of 23° C. for 24 hours, more than 0.5 g of the immersed polymer does not dissolve in the water.

Examples of water-soluble polymers having a coating formation ability include naturally-occurring macromolecules such as pullulan, hyaluronic acid, chondroitin sulfate, poly-γ-glutamic acid, modified corn starch, β-glucan, glucooligosaccharide, mucopolysaccharide such as heparin and keratosulfate, cellulose, pectin, xylan, lignin, glucomannan, galacturonic acid, psyllium seed gum, tamarind seed gum, gum arabic, gum traganth, water-soluble soybean polysaccharide, alginic acid, carrageenan, laminaran, agar (agarose), fucoidan, methyl cellulose, hydroxypropyl cellulose, hydroxypropyl methyl cellulose; and synthetic macromolecules such as partially saponified polyvinyl alcohol (when not used in combination with a cross-linking agent), low saponified polyvinyl alcohol, polyvinyl pyrrolidone (PVP), polyethylene oxide, and sodium polyacrylate. These water-soluble polymers can be used alone or in combination of two or more. It is preferable to use pullulan and the synthetic macromolecules such as partially saponified polyvinyl alcohol, low saponified polyvinyl alcohol, polyvinyl pyrrolidone, and polyethylene oxide, of these water-soluble polymers, from the viewpoint of easily manufacturing the coating. When polyethylene oxide is used as the water-soluble polymer, its number average molecular weight can be preferably 50,000 or more and 3,000,000 or less, and more preferably 100,000 or more and 2,500,000 or less.

On the other hand, examples of the water-insoluble polymers having a coating formation ability can include completely saponified polyvinyl alcohol, which can be insolubilized after the formation of a coating; partially saponified polyvinyl alcohol, which can be cross-linked after the formation of a coating when used in combination with a cross-linking agent; oxazoline modified silicone such as a poly(N-propanoylethyleneimine)-grafted dimethylsiloxane/ γ-aminopropylmethylsiloxane copolymer; polyvinylacetal diethylamino acetate; zein (main component of corn proteins); polyester; polylactic acid (PLA); an acrylic resin such as a polyacrylonitrile resin or a polymethacrylic acid resin; a polystyrene resin; a polyvinyl butyral resin; a polyethylene terephthalate resin; a polybutylene terephthalate resin; a polyurethane resin; a polyamide resin; a polyimide resin; and a polyamideimide resin. These water-insoluble polymers can be used alone or in combination of two or more. It is preferable to use completely saponified polyvinyl alcohol, which can be insolubilized after the formation of a coating, partially saponified polyvinyl alcohol, which can be cross-linked after the formation of the coating when used in combination with a cross-linking agent, a polyvinyl butyral resin, oxazoline modified silicone such as a poly(N-propanoylethyleneimine)-grafted dimethylsiloxane/γ-aminopropylmethylsiloxane copolymer, water-soluble polyester, zein, and the like, of these water-insoluble polymers.

The content of the component (a) in the composition can be preferably 50 mass % or more, more preferably 55 mass % or more, and even more preferably 60 mass % or more. In addition, the content of the component (a) in the composition can be preferably 98 mass % or less, more preferably 96 mass % or less, and even more preferably 94 mass % or less. The content of the component (a) in the composition can be preferably 50 mass % or more and 98 mass % or less, more preferably 55 mass % or more and 96 mass % or less, and even more preferably 60 mass % or more and 94 mass % or less. When the component (a) is blended into the composition in this proportion, the composition can sufficiently volatilize, for instance, when the electrostatic spraying method is performed.

On the other hand, the content of the component (c) in the composition can be preferably from 4 to 34 weight %, more preferably from 6 to 30 weight %, and even more preferably from 8 to 18 weight %. When the component (c) is blended into the composition in this proportion, a desired coating can be successfully formed.

The component (b) can be preferably contained from the viewpoint of conductivity of the liquid agent, and the content can be preferably 10% or less, more preferably 5% or less with respect to the component (a), from the viewpoint of spinnability, preferably the content can be 0.5% or more.

For example, the composition can be comprised of a volatile solvent selected from alcohol and ketone, polymer with fiber forming ability, and water, preferably alcohol, water insoluble polymer, and water, more preferably ethanol, polymer with fiber forming ability selected from polyvinyl butyral, polyurethane, and partially saponified polyvinyl alcohol, and water. The water insoluble polymer with fiber forming ability can be comprised of the selection of one or more completely saponified polyvinyl alcohol, which can be insolubilized after the fiber formation; partially saponified polyvinyl alcohol, which can be cross-linked after the fiber formation when used in combination with a cross-linking agent; oxazoline modified silicone such as a poly(N-propanoylethyleneimine)-grafted dimethyl siloxane/γ-aminopropylmethylsiloxane copolymer; polyvinylacetal diethylamino acetate; zein (main component of corn proteins); polyester; polylactic acid (PLA); an acrylic resin such as a polyacrylonitrile resin or a polymethacrylic acid resin; a polystyrene resin; a polyvinyl butyral resin; a polyurethane resin; a polyethylene terephthalate resin; a polybutylene terephthalate resin; a polyurethane resin; a polyamide resin; a polyimide resin; and a polyamideimide resin, and the like. Optionally, the solution can contain greater than 70% alcohol.

The water insoluble polymer with fiber forming ability can be preferably comprised of one or more partially saponified polyvinyl alcohol, which can be cross-linked after the fiber forming when used in combination with a cross-linking agent, a polyvinyl butyral resin, a polyurethane resin; oxazoline modified silicone such as a poly(N-propanoylethyleneimine)-grafted dimethylsiloxane/γ-aminopropylmethylsiloxane copolymer, water-soluble polyester, zein, and the like.

One or more embodiments of the disclosed subject matter can involve application of a cosmetic, such as a base/foundation, a concealer, a moisturizer, and coloring. Of course, embodiments of the disclosed subject matter are not limited to application of cosmetics. For example, one or more embodiments of the disclosed subject matter can involve application of deodorants, scents, sun protection, creams, topical drug delivery, anti-microbial barriers and coatings, hydrophobic/phallic surface treatments, anti-fouling coatings, tissue repair, etc.

Turning to the figures, FIG. 1 shows a system 100 according to one or more embodiments of the disclosed subject matter. System 100 can be comprised of a base station 200 and a handset 300. Optionally, the base station 200 and the handset 300 may be connected to each other via a transmission medium 400, which may provide power from the base station 200 to the handset 300 and communications between the base station 200 and the handset 300.

The transmission medium 400 may be a plurality of wired transmission lines, for instance, separately insulated inside a single transmission cord or separate transmission cords, where one of the wired transmission lines can transmit relatively high voltage from the base station 200 to the handset 300 and another transmission line (or lines) can provide relatively low voltage, communication signals, and grounding for the handset 300. Thus, in one or more embodiments, the low voltage transmission can be implemented via a low voltage cable bundle for power and communications to the handset 300 (e.g., for a motor and/or controller of the handset 300); a ground cable may be integrated into the low voltage cable bundle or, alternatively, the ground cable may be a separate cable. Alternatively, some or all of the signals can be transmitted wirelessly between the base station 200 and the handset 300.

Generally, for electrospinning or electrospraying, the surface on which the fibers or droplets, respectively, are to be deposited on should or must be at or near ground potential. As such, the deposit surface, such as skin of a user, should be grounded during the electrospinning or electrospraying process. In terms of grounding a user, this may be accomplished by grounding the user to the base station 200, the handset 300, or some other structure. For example, the user may be grounded via a grounding strap 501 attached to the user and a grounding line 500 connected to the base station 200, such as shown in FIG. 1, via a grounding strap (not expressly shown) attached to the user and a grounding line 502 connected to the handset 300, via a rod or a plate on a grip of the handset 300 and optionally a grounding strap attached to the user, or via a grounding route separate from the base station 200 and the handset 300, such as a grounding route integrated into a chair, seat, table, metal plate, or other structure. Also, in the case of someone other than the user (e.g., an esthetician) using the handset 300 to apply the electrospun or electrosprayed solution to the user, the other person may also be grounded, for example, via the handset 300 or a separate grounding route, such as described above.

The base station 200 can include a control panel 202 and circuitry, which may include a controller or controllers 204 and/or a power source 206. Optionally, the circuitry can include computer-readable memory (not expressly shown) configured to store settings and/or programming code executable by the controller 204, to control the power source 206, the control panel 202, and the handset 300. In one or more embodiments, the base station 200 may include a handset receptacle 208 configured to receive and physically hold or stow the handset 300. Optionally, the base station 200 may include a timer settable and viewable by the user, for instance. In one or more embodiments of the disclosed subject matter, the base station 200 may have relatively less functionality than described above. For example, the base station 200 may simply have the handset receptacle 208 and therefore act only as a holder or receptacle for the handset 300.

The control panel 202 may be configured to receive control inputs to control the handset 300 and the base station 200 by way of the controller 204, for instance. For example, the control panel 202 may have a control input to control high voltage to the handset 300, a control input to control motor direction of a motor (e.g., stepper motor) of the handset 300, and/or a control input to control flow rate of the handset 300 (e.g., speed of the motor of handset 300). The control panel 202 may also have a power on/off control input to control an on/off state of the base station 200 and, optionally, whether some or all of the voltage and communication signals are supplied to the handset 300. The user input interfaces can be knobs, switches, buttons, a touch panel or screen, or a combination some or all of the foregoing. Further, such user input interfaces may identify relatively simple predetermined settings for various operational characteristics controllable by the user via the control panel 202.

Optionally, control panel 202 may include a display (not expressly shown), such as a liquid crystal display (LCD) or Light Emitting Diode (LED) display, which may be a touch screen or panel, as noted above. The display may output information corresponding to operating characteristics of the handset 300, such as flow rate, an amount of high voltage received by the handset 300 or otherwise applied to the solution to perform electrospinning or electrospraying, a status of the handset 300, a direction of the motor of the handset, and/or whether appropriate grounding of the user is provided. Additionally or alternatively, the display may output information corresponding to operating characteristics of the base station 200, such as an amount of high voltage supplied to the handset 300, the on/off state, whether the handset 300 is detected by the base station 200 to be docked in the handset receptacle 208, and/or whether power is supplied to the base station 200 by an internal or external power source.

The power source 206 may be or include a relatively low voltage power source, such as 9 VDC supplied from an onboard power source (e.g., a battery or batteries) or an external source, such as mains (e.g., from a wall electrical receptacle), in which case the voltage would be converted from AC to the relatively low DC voltage, or an external battery unit. Of course, in the case of mains, the power source 206 can have an AC/DC converter to convert the mains to the relatively low voltage. Generally, components of the base station 200, such as the control panel 202 and the controller 204, may be supplied power from the power source 206, particularly the relatively low voltage.

Optionally, the power source 206 may be or include a relatively high voltage power source to provide a corresponding high voltage to the handset 300. The power source 206 may have or be coupled to a transformer that converts a relatively low voltage, such as the above-referenced 9 VDC, to the relatively high voltage, particularly a relatively high DC voltage. The high voltage should be sufficiently high to create an electric field that can generate a Taylor cone of the solution; also a current supply sufficient to charge up the solution and also overcome parasitic losses/capacitances should be supplied. Thus, in embodiments of the disclosed subject matter, the power source 206 can produce high voltage with sufficient current output to perform a desired electrospin or electrospray operation. The high DC voltage may be preferably about 14 kV DC; more preferably about 6 kV DC to about 30 kV DC; even more preferably about 11 kV DC to about 14 kV DC; and most preferably about 10 kV DC to about 16 kV DC. Optionally, the high voltage may be controllable using the control panel 202, for instance, preferably about 6 kV DC to about 30 kV DC; even preferably from about 11 kV DC to about 14 kV DC; and even more preferably about 10 kV DC to about 16 kV DC.

The relatively high voltage HV can be supplied to the handset 300 via the transmission medium 400, under control of the control panel 202 and controller 204, for instance. Further, the relatively high voltage can be provided to the handset 300 to generate an electric field (EF) in and around a solution contained in the handset 300 to output the solution in electrospun or electrospray format. Alternatively, the high voltage power source may be provided in the handset 300.

Incidentally, the transmission medium 400 (or portions thereof) may be removably coupled to the base station 200. Thus, different handsets, such as handset 300, may be coupled to the same base station 200. The control panel 200 may be used to control settings, configurations, etc. based on the particular handset coupled to the base station 200. Optionally, the base station 200 may detect the type of handset and automatically set some or all settings, configurations, etc. based on the detected type. Alternatively, the base station 200, via the control panel 202, may display options so the user may set the settings, configurations, etc. based on the particularly type of handset. Likewise, the grounding line 500 may be removably coupled to the base station 200.

Alternatively, the system 100 may be comprised of the handset 300 and not the base station 200. That is, in one or more embodiments, components of the base station 200 may be implemented in the handset 300 such that the handset 300 can be fully operational as a stand-alone electrospinning or electrospraying apparatus. For example, the handset 300 can have a power source to provide a high voltage HV to perform the electrospinning or electrospraying process and a power source to provide relatively low voltage (e.g., 9 VDC) to power other components of the handset 300, such as an electric motor of the handset 300. Optionally, the transmission medium 400 may still be coupled to the handset 300, for instance, to provide power from mains (e.g., a wall receptacle). Of course, in the latter case the transmission medium 400 may not need to accommodate relatively high voltage, since such high voltage is now provided by the handset 300. Alternatively, the handset 300 may be powered locally, using a battery or batteries directly coupled to or in the handset 300.

The handset 300 can be comprised of a body assembly 310 and an output assembly 350. The output assembly 350 can be removably coupled to the body assembly 310, for instance, using a snap-fit connection or connections. The output assembly 350 can have an outlet or nozzle 352 or, alternatively, be coupled to the nozzle. Optionally, whether the nozzle 352 is considered part of the output assembly 350 or a different component thereof, such nozzle 352 may be removably coupled to the body assembly 310. Generally, the user can provide a control input to the body assembly 310 to cause a high voltage HV and thus a corresponding electric field to be applied in and around solution in the output assembly 350, such that the solution is output in electrospun or electrospray fashion from the nozzle 352.

The body assembly 310 may be deemed a durable, and the output assembly 350 may be deemed a consumable, in that the body 310 assembly may be used over and over again, whereas some or all of the output assembly 350 can be consumed and thus replaced. Of course, the body assembly 310 may itself have consumables, such as a battery or batteries. Put another way, the "consumable" portion of the handset 300 may be implemented in one of two ways: a single use configuration whereby the entire output assembly 350 is removable and replaceable with another entire output assembly 350, or a multi-use configuration whereby only a portion of the output assembly 350, for instance, a consumable housing (e.g., carpule) or solution container portion thereof, may be removed and replaced with another consumable housing or solution container portion.

The output assembly 350 can contain the solution, for instance, in a container (e.g., a carpule, cartridge, etc.). When the container is empty or if another type of solution is desired, the entire output assembly 350 may be removed from the body assembly 310 and another output assembly 350 provided in place. Alternatively, in one or more embodiments, only a portion of the output assembly 350 may be replaced, such as only the container.

Figure 2A:
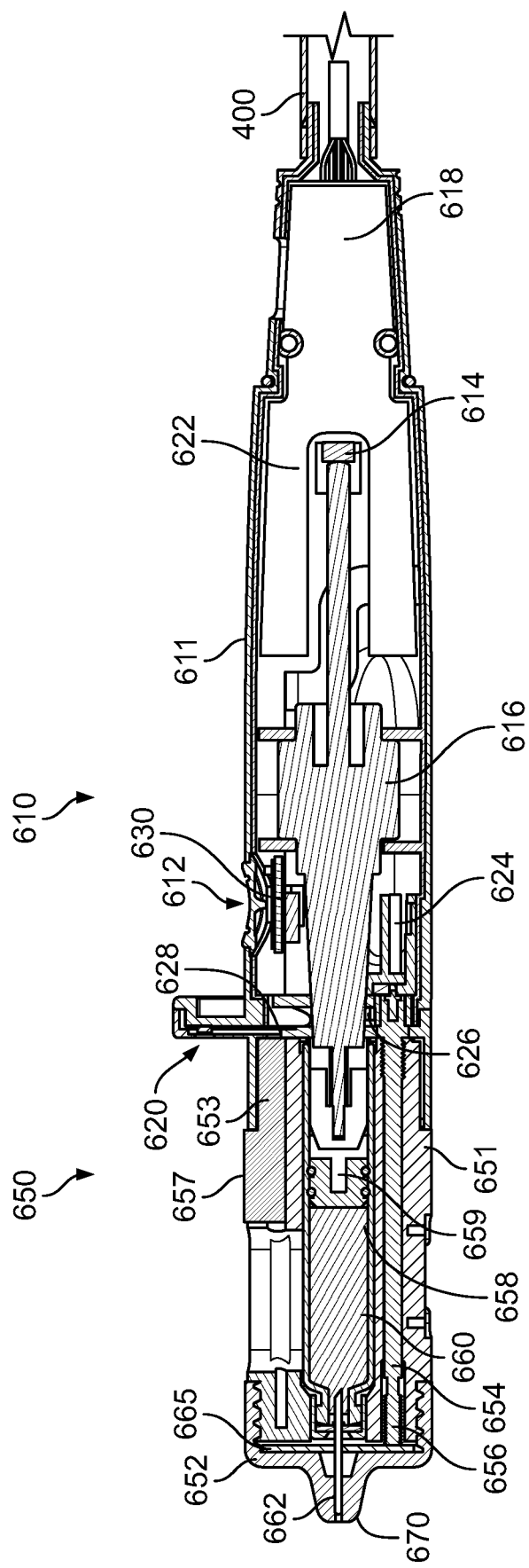
FIG. 2A is a sectional view of an example of a hand-held device according to one or more embodiments of the disclosed subject matter.
Figure 2B:
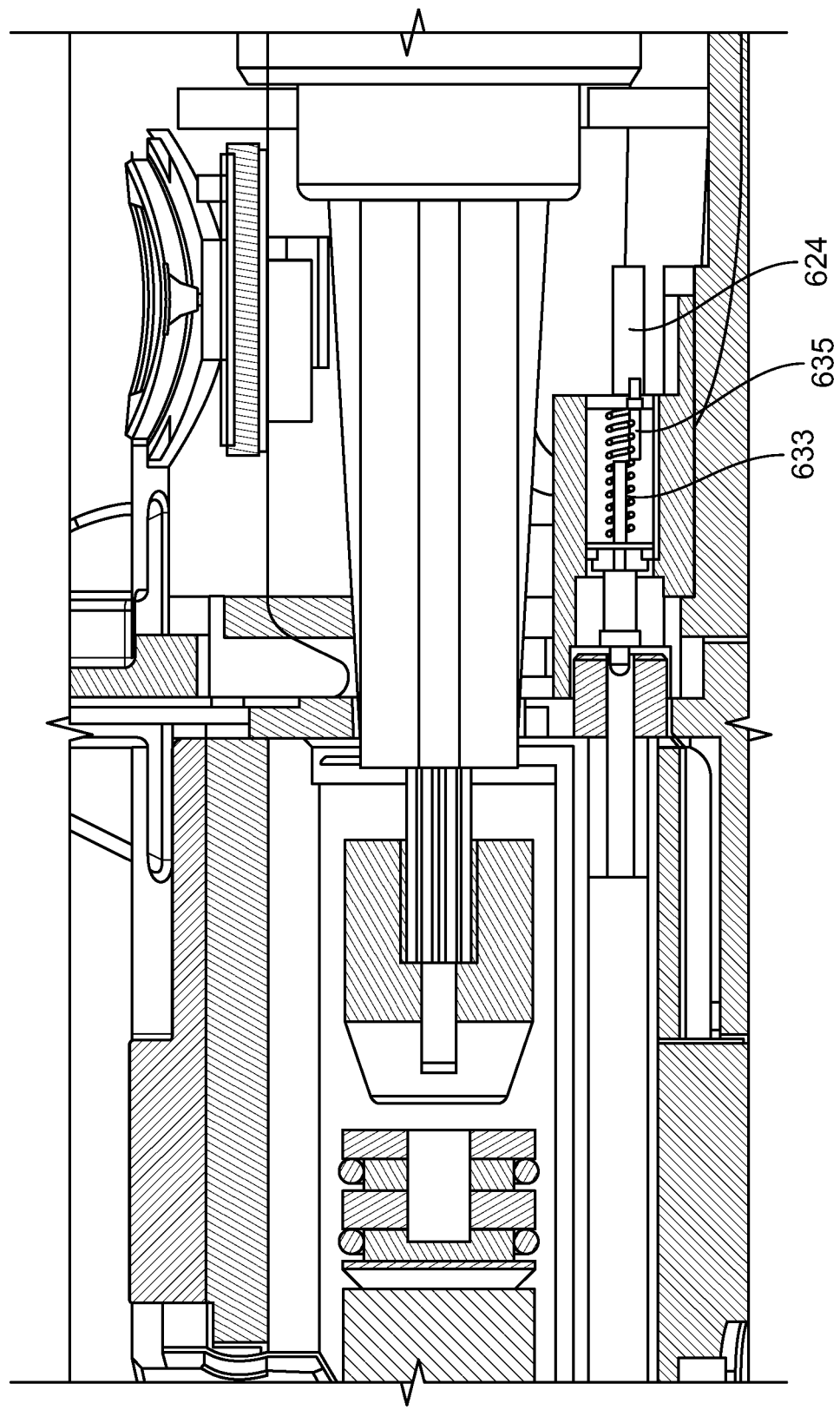
FIG. 2B is an enlarged view of a portion of the hand-held device of FIG. 2A.

FIG. 2A is a sectional view of a non-limiting example of a handset 600 (i.e., portable, hand-held device) according to one or more embodiments of the disclosed subject matter, configured to output an electrospun or electrosprayed solution stored in the handset 600. FIG. 2B is an enlarged view of a portion of the hand-held device of FIG. 2A. More specifically, the portion shown in FIG. 2B can represent a lock.

The handset 600 can be comprised of a body assembly 610 and an output assembly 650. The output assembly can have or be coupled to an output or nozzle 652. That is, the nozzle 652 may be part of the output assembly 650 or considered a separate component from the nozzle 652. Optionally, the body assembly 610 may be coupled to the transmission medium 400, which, in turn, may be coupled to a base station, such as the base station 200.

The body assembly 610 can be comprised of a housing 611, a user control interface 612, a drive, which may include a motor 614 and an actuator 616, a high voltage HV connector 624 configured to provide high voltage HV to the output assembly 650, and circuitry 618 configured to control various aspects, operations, and functions of the body assembly 610 and the handset 600 as a whole. Optionally, the body assembly 610 may have a distance sensor 620 configured to determine distance of the handset 600, for instance, a nozzle tip 670, away from a deposit surface. Optionally, the body assembly 610 may have a solution fill level detector 622. Optionally, the body assembly 610 may have a consumable detector configured to detect whether the output assembly 650 is properly connected to the body assembly 610. Optionally, the body assembly 610 may have a light source 628 configured to output light for a feedback indicator, such as a feedback indicator 657 of the output assembly 650; additionally or alternatively, the body assembly 610 may have its own one or more feedback indicators, configured to provide visual and/or audible feedback to the user. Optionally, the body assembly 610 may have a haptic feedback mechanism 630 configured to provide haptic feedback to the user, such as vibration and/or tapping. The components of the body assembly 610 are described in more detail below. The feedback indicator 657 may be based on signals from the distance sensor 620. Alternatively, a visual-based system may be used as so-called feedback to determine suitable distance(s) of the handset 600, particularly the nozzle tip 670, away from the deposit surface. A visual-based system may implement intersecting lights (e.g., lasers) to assist the user identify a suitable positioning for the nozzle tip 670 relative to the deposit surface.

The output assembly 650 can be comprised of a housing 651; the feedback indicator 657; a conducting rod 654; a high voltage connector 656; a consumable housing 658, which may include a bung 659 and a solution container 660 that contains solution; a needle electrode 662; and, of course, the nozzle 652. Optionally, the output assembly 650 may also include an electrode 665, which may be a disc electrode, a plate-shaped electrode, or a flange electrode (hereinafter "disc electrode 665"). As set forth herein, the needle electrode 662 may be termed a primary electrode, and the disc electrode 665 may be deemed a secondary electrode. The components of the output assembly 650 are described in more detail below.

The following paragraphs provide more detailed description regarding select components of the body assembly 610.

The user control interface 612 of the body assembly 610 may be in the form of a trigger or a switch (illustrated in FIG. 2A), for instance, a tactile switch or trigger. The user control interface 612 can be activated by user input, for instance, a user's finger or thumb, to activate the handset 600. Specifically, the user control interface 612 can be activated by the user to activate the motor 614 to output the solution to the nozzle 652 and output therefrom, to activate the high voltage HV to create a corresponding electric field for application to the solution, or both. Generally, the user control interface 612 may be provided far enough away from the nozzle 652 to prevent interference, for instance. As a non-limiting example, the user control interface 612 may be about 44 mm from the nozzle 652. As shown in FIG. 2A, for instance, no portion of the control interface 612 may overlap the output assembly 650 (or the consumable housing 658) in a top plan view of the body assembly 610.

Optionally, the user control interface 612 may be a multi-stage user interface, such as a half/full press tactile switch or trigger. Thus, for example, the first stage may be to check the settings of the handset 600, for instance, to identify whether the handset 600 is suitably positioned—i.e., not too far away and/or not too close—relative to the deposit surface (e.g., skin of the user). That is, the first stage may be used to for depth adjustment of the handset 600 before outputting the electrospun or electrosprayed solution. The second stage may be to cause output of the electrospun or electrosprayed solution by controlling the motor 614 and the high voltage applied to and around the solution.

Generally, too far away may be defined as greater than about 120 mm, preferably about 110 mm or greater. For example, about 110 mm to about 120 mm may be deemed too far away, and greater than 120 mm may be deemed precariously too far away, for instance, where substandard or defective electrospraying or electrospinning can occur. Generally, too close may be defined as closer than about 30 mm, preferably about 40 mm or closer. For example, about 30 mm to about 40 mm may be deemed too close, and closer than about 30 mm may be deemed precariously too close, for instance, in terms of the high voltage HV relative to the deposit surface. Thus, an acceptable threshold may be about 40 mm to about 50 mm and/or about 100 mm to about 110 mm, preferably about 50 mm to about 100 mm, for instance.

Optionally, an indicator, such as a particular color of light, may be output by the handset 600 depending upon a setting or settings of the handset 600. The solution can be output from the nozzle 652 when the user activates the second stage of the user control interface 612. Optionally, the second stage can also activate application of the high voltage HV to the solution, as eluded to above.

The motor 614 of the drive may be a stepper motor, for instance, that drives the actuator 616, which may be a linear actuator. The motor 614 and actuator 616 can be controlled based on operation of the user control interface 612. Generally speaking, actuation of the actuator 616 can drive a plunger relative to a solution container (described in more detail later) to cause the solution to be output from the solution container 660 to the nozzle 652 for application of high voltage HV and output from the nozzle 652 as electrospun or electrosprayed solution. Optionally, the motor may be programmable, for instance, using the circuitry 618. Such programming may provide for different flow profiles to be used based on particular application conditions, such as environment, type of solution to be applied, high voltage HV applied, etc. Optionally, the actuator 616 can be controlled, prior to an electrospinning or electrospraying operation, to prime the handset 600 by removing air from the solution flow path.

The motor 614 and actuator 616 may not provide back suction. That is, in one or more embodiments, back suction of the solution may not be provided. Alternatively, the motor 614 and actuator 616 may be controlled to provide back suction, for instance, for a predetermined duration of time. The predetermined duration of time may be preferably about 0.1 seconds; more preferably about 0.5 seconds, after stopping output of the solution from the nozzle 652.

The circuitry 618 may be comprised of a power supply (not expressly shown), which may provide low and high voltage to respective components of the handset 600, and a high voltage connector 624 configured to provide the high voltage HV to the output assembly 350 to create a corresponding electric field for application to the solution at the nozzle 652.

Optionally, at least a portion of the circuitry 618 may be implemented via a printed circuit board (PCB). The PCB may be arranged as shown in FIG. 2A, for instance. Alternatively, the PCB may be arranged in the output assembly 650. Such arrangement may be to facilitate placement of a distance sensor, such as distance sensor 620 and/or a handset status indicator as part of the output assembly 650. Further, in such a case, the PCB may not be removable from the output assembly 650. That is, in such a case, a portion of the output assembly 650, such as a container for solution, may be removed and replaced.

The high voltage connector 624 may be a spring-loaded pogo connector, which may be operative to have supplied the high voltage HV thereto only when the output assembly 650 is properly coupled to the body assembly 610. That is, the spring-loaded pogo connector may make contact with a female component of the circuitry 618 essentially to complete or close the high voltage circuit and disconnect from the female component to open the high voltage circuit, when the output assembly 650 is not coupled to the body assembly 610.

The circuitry 618 may also be comprised of the solution fill level detector 622. Alternatively, the solution fill level detector 622 may be deemed a separate component or components from the circuitry 618. The solution fill level detector 622 may include or may be implemented using a Hall effect sensor array, such as illustrated in FIG. 2A.

For example, the Hall effect sensor array can detect a position of the actuator 616. As an example, a 100% filling level may be detected as a home position of the actuator 616, a 15% filling level may be detected as 15% remaining from an end position of the actuator 616, and a filling level of about 0% or about 1% may be detected as the end position of the actuator 616 (i.e., the full travel stroke reached). Optionally, when 1% or 0% is detected, the actuator 616 may be controlled to retract, for instance, to the home position, and/or the user control interface 612 may be deactivated. Such control may be performed using the circuitry 618. Different indicators on the handset 600 may be used to identify a detected fill state or level of the solution container 660. For example, when a detected filling level is above a predetermined threshold an indicator, such as a light source, may be constantly illuminated. Optionally, the light source may additionally or alternatively output a particular color showing the fill level. When the detected fill level is at or below the threshold (and optionally above another threshold), the indicator may change. For example, the indicator may pulse. In such a case, the color of the light may change or, alternatively, the color may stay the same. When the detected fill level reaches the another threshold, the indicator may change. For instance, the indicator may pulse more rapidly and/or change in color. The foregoing are merely examples and not intended to limit fill level indications or corresponding actions that may be provided according to one or more embodiments of the disclosed subject matter based on the detected fill level.

The circuitry 618 may also be comprised of the distance sensor 620. Alternatively, the distance sensor 620 may be deemed a separate component or components from the circuitry 618. The distance sensor 620 can be arranged as shown in FIG. 2A, for instance. Alternatively, the distance sensor 620 can be provided in or at the output assembly 650. Generally, the distance sensor 620 can determine distance of the handset 600, for instance, the nozzle 652, from a deposit surface. Signals from the distance sensor 620 can be provided to control operations of the handset 600. For example, signals from the distance sensor 620 can be provided to the circuitry 618 to control, for instance, disable, the motor 614 and/or the user control interface 612. That is, optionally, based on signals from the distance sensor 620, the handset 600 can automatically shut off the high voltage HV supply to the electrode. Such control may be performed when signals from the distance sensor 620 indicate that the handset 600 is positioned too far away from and/or too close to the deposit surface. The signals from the distance sensor 620 can also be processed by the circuitry 618 to identify whether the handset 600 is suitably positioned relative to the deposit surface and therefore allow operation of the handset 600 to output electrospun or electrosprayed solution to the deposit surface.

Figure 4:
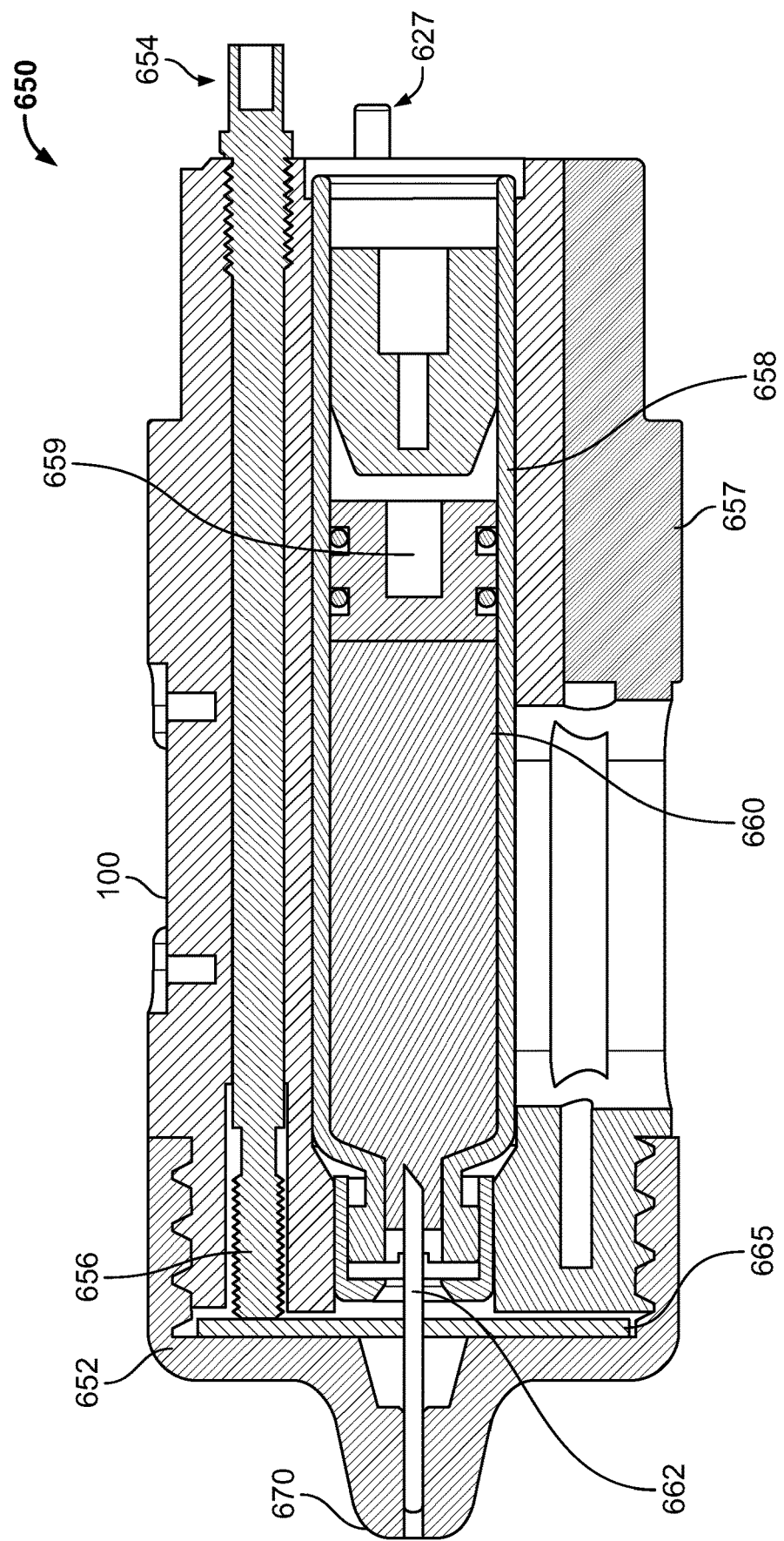
FIG. 4 is a sectional view of a consumable portion of the hand-held device of FIG. 2A, according to one or more embodiments of the disclosed subject matter.

The body assembly 610 may also have a consumable detector 626, which may include a switch. Optionally, the consumable detector 626 may be part of the circuitry 618. Alternatively, the consumable detector 626 may be may be deemed a separate component or components from the circuitry 618. The consumable detector 626 can detect whether the output assembly 650 is properly connected to the body assembly 610. For example, when the output assembly 650 is properly connected to the body assembly 610, the consumable detector 626 may output a signal or signals to indicate that the output assembly 650 is coupled to the body assembly 610. Optionally, such signal(s) may control the feedback indicator 657 on the body assembly 610 and/or the output assembly 650 to output an indication of such proper coupling. Additionally or alternatively, such signal(s) may allow activation of the user control interface 612 and/or high voltage HV supply to the electrode. Conversely, absence of the signal(s) may cause deactivation of the user control interface 612 and/or the high voltage HV supply to the electrode. Optionally, the consumable detector 626 include or interface with a safety locking pin 627 (example shown in FIG. 4) configured to engage with a corresponding receptacle of the body assembly 610 (not shown) to better ensure the output assembly 650 is in place relative to the body assembly 610 before the high voltage HV is activated and provided to the output assembly 650. Though FIG. 4 shows a safety lock in the form of locking pin 627, such safety lock may take other forms, such as flange, shoulder, corner, and/or edge keyed geometric configurations. Additionally or alternatively, optionally, the safety lock may include a pressing member 633 and a pressed member 635, such as shown in FIG. 2B. Generally, the pressing member 633 (e.g., a pin) on the output assembly 350, when properly connected to the body assembly 310, can contact and press the pressed member 635 to displace the pressed member 635 to complete a circuit for high voltage to be supplied.

The body assembly 610 may have a light source 628, such as one or more lights. Optionally, the light source 628 may be comprised of one or more light emitting diodes (LEDs). Optionally, the light source 628 may be part of the circuitry 618. Alternatively, the light source 628 may be may be deemed a separate component or components from the circuitry 618. The light source 628 may be configured to output light, in controlled fashion, to an indicator, which may be provided as part of the body assembly 610 or as part of the output assembly 650, as illustrated in FIG. 2A. Further, the light source 628 may be controlled to output light, for instance, a specific color and/or consistency, based on signals from the consumable detector 626, the distance sensor 620, and/or the user control interface 612. Optionally, the light source 628 can output different colors of light individually, at one time, based on signals from the consumable detector 626, the distance sensor 620, and/or the user control interface 612.

Optionally, the body assembly 610 may have a haptic feedback mechanism 630. The haptic feedback mechanism may include a vibration motor, for instance. The haptic feedback mechanism 630 may provide feedback in the form of vibration and/or tapping. Such feedback may be based on how far away the handset 600 is detected to be from the deposit surface, as sensed by the distance sensor 620, for instance. For example, the haptic feedback mechanism 630 may start providing feedback when the handset 600 crosses a first predetermined distance threshold. The haptic feedback mechanism 630 may transition to a different feedback upon crossing a second predetermined distance threshold. For instance, the haptic feedback mechanism may start vibrating when the first predetermined distance threshold is crossed, then vibrate more strongly, or according to a different pattern, when the second predetermined distance threshold is crossed. Further, the predetermined distance thresholds can be according to a moving direction of the handset 600 going closer to the deposit surface and, separately, according to a moving direction of the handset 600 going farther away from the deposit surface.

The following paragraphs provide more detailed description regarding select components of the output assembly 650. Further, FIGS. 4-7, which show various aspects of the output assembly 650 in greater detail, may be referenced.

As noted above, the output assembly 650 can be comprised of the housing 651; the feedback indicator 657; the conducting rod 654; the high voltage connector 656; the consumable housing 658, which may include the bung 659 and the solution container 660 that contains solution; the needle electrode 662; optionally the nozzle 652; and optionally the disc electrode 665. FIGS. 3-7 show the output assembly 650 in more detail.

Figure 3:
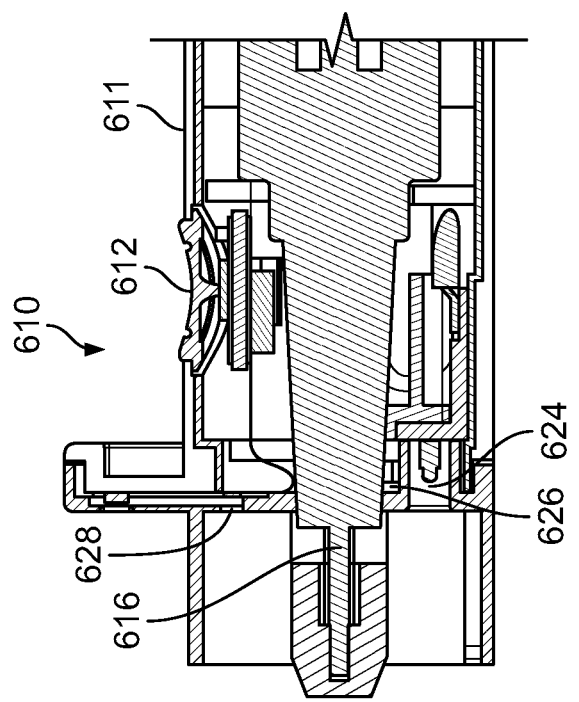
FIG. 3 shows an exploded sectional view of portions of the hand-held device of FIG. 2A.
Figure 3:
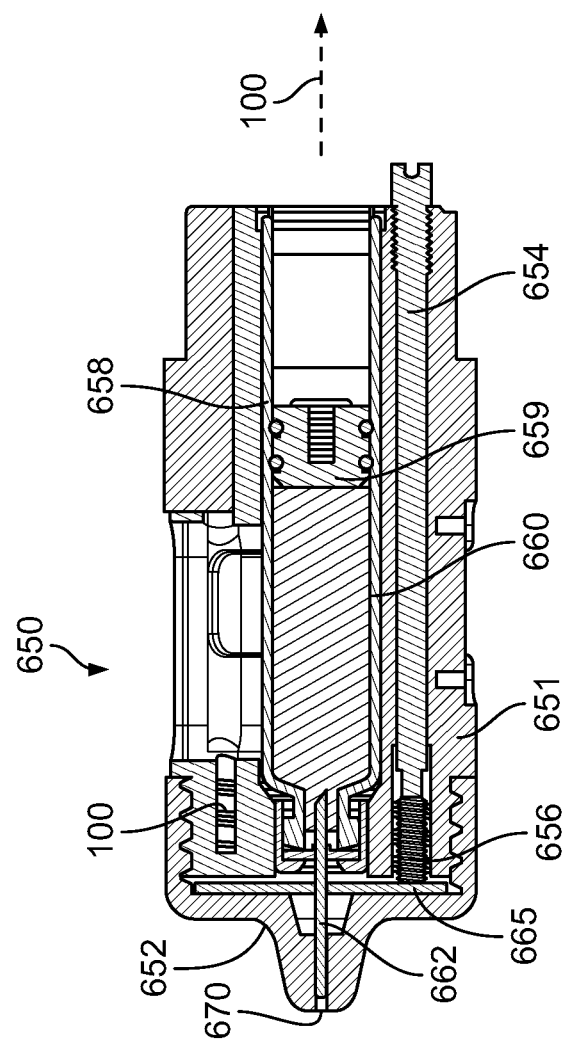
Figure 6:
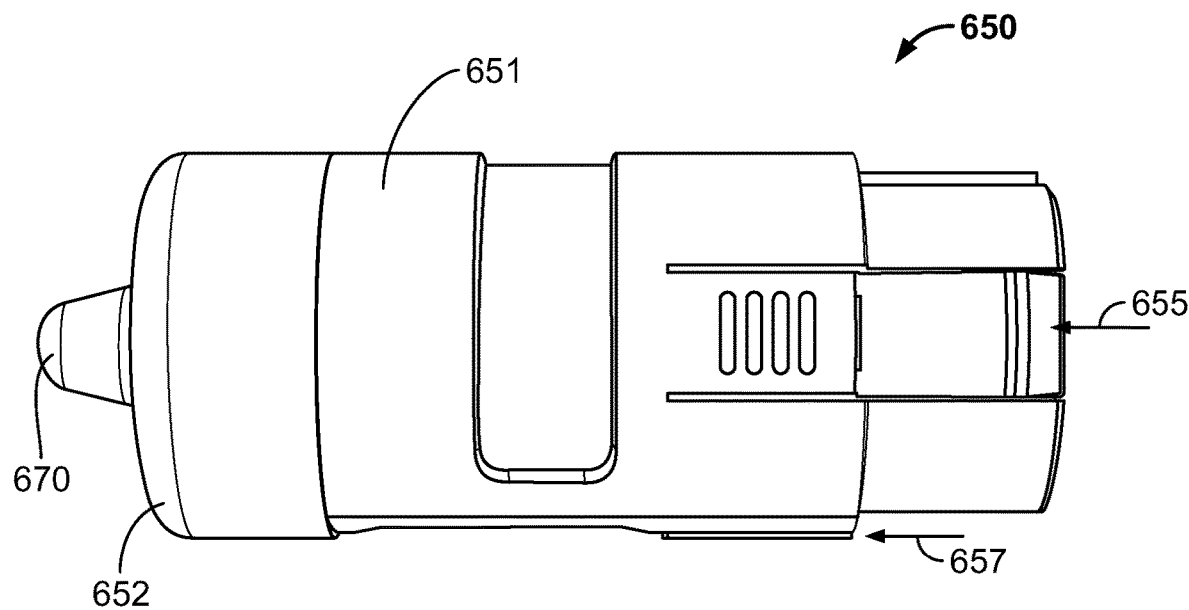
FIG. 6 is a side view of the consumable portion of FIG. 4.
Figure 7:
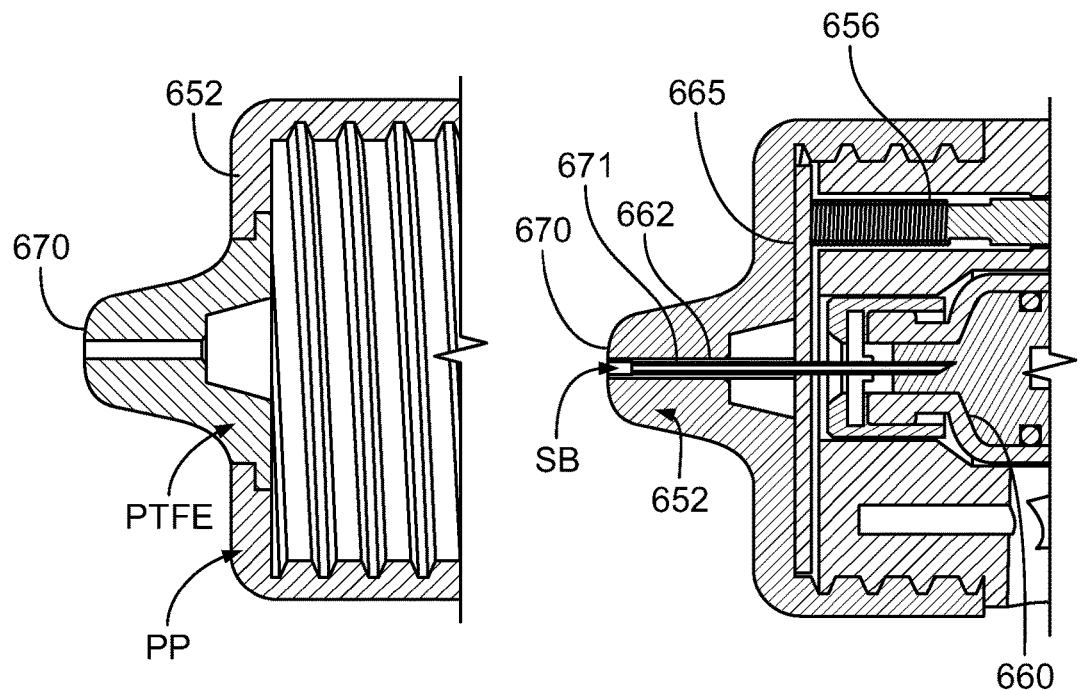
FIG. 7 shows side and sectional views of a nozzle portion of the hand-held device of FIG. 2A, according to one or more embodiments of the disclosed subject matter.
Figure 8:
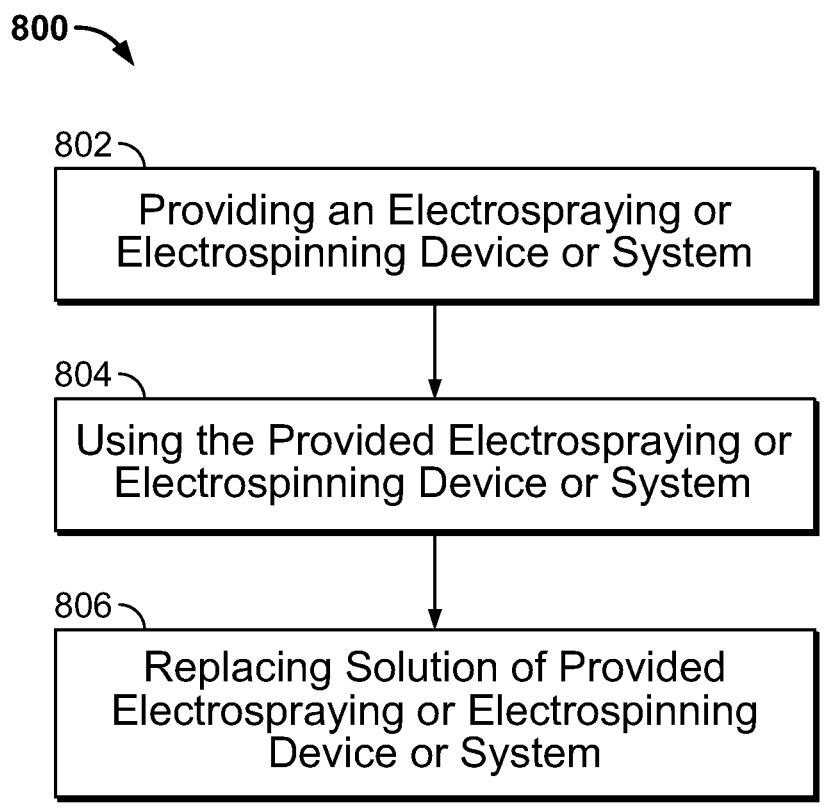
FIG. 8 is a basic flow diagram of a method according to one or more embodiments of the disclosed subject matter.

As shown in FIG. 3, the output assembly 650 can be removably coupled (i.e., connected and disconnected) to the body assembly 610, for instance, using a snap-fit or clip-on connection or connections. The output assembly 650 may be removed and replaced with another output assembly 650, for instance, when the solution container 660 in the replaced output assembly 650 is empty of solution or reduced to a predetermined fill level amount. FIG. 6 shows an example of a clip-on connector 655 (opposite connector not shown) that can be received by a corresponding receptacle of the body assembly 610. The connector 655 (and its opposing connector) may be depressed inwardly to release the output assembly 650 from the body assembly 610.

Such coupling of the output assembly 650 with the body assembly 610 can provide power, particularly the high voltage HV, to the output assembly 650 to create the electric field to be applied to the solution to output the solution in electrospun or electrospray fashion. In particular, proper coupling of the output assembly 650 with the body assembly 610 can include an end of the conducting rod 654, which may be made of a conductive material, such as metal (e.g., stainless steel, brass) being received by the HV connector 624, such that high voltage HV can be provided to the conducting rod 654 and thus the needle electrode 662 and disc electrode 665, when present, since the conducting rod 654 can contact the disc electrode 665 using a spring-loaded connection, for instance. Optionally, when high voltage HV is supplied to the HV connector 624, the high voltage can be continuously supplied, i.e., not pulsed or varied during a particular electrospinning or electrospraying operation. Of course, the high voltage HV supplied to the HV connector 624 can be changed from electrospinning/electrospraying operation to electrospinning/electrospraying operation, for instance, by using the control panel 202 of the base station 200. Also, a boss of the actuator 616 may be received in a recess of the consumable housing 658, such that the boss abuts the bung 659 and can act on the bung 659 to cause the bung 659 to move inside the consumable housing 658 and output solution to the needle electrode 662 and from the nozzle 652.

The output assembly 650 may have a feedback indicator 657; additionally or alternatively, the feedback indicator 657 may be part of the body assembly 610. The feedback indicator 657 may be configured to provide a visual output to the user, for instance, of a status or characteristic of the handset 600. For example, the feedback indicator 657 may include a light path 653 operatively coupled to the light source 628 such that light from the light source 628 can be output at the feedback indicator 657. Additionally or alternatively, one or more additional feedback indicators may be provided (not shown) to provide feedback in the form of audio feedback. For example, one or more speakers may be provided. The circuitry 618 may be configured to output saved prerecorded messages regarding the status of the handset 600, such as whether the handset 600 is positioned correctly or not in terms of distance from the deposit surface, whether the solution container 660 is empty, whether the handset 600 is ready (or not ready) for electrospinning or electrospraying operation, etc.

The consumable housing 658 may include the bung 659 and the solution container 660 that contains solution. As noted above, a boss of the actuator 616 may be received in a recess of the consumable housing 658, such that the boss abuts the bung 659. The boss can act on the bung 659, by way of movement of the actuator 616, to cause the bung 659 to move inside the consumable housing 658 and cause solution to be pushed toward and into the needle electrode 662 and ultimately output from the nozzle 652. The solution can be stored in the consumable housing 658 in a manner that limits atmospheric exposure until usage. For example, when the solution is to be used, a rear portion of the needle electrode 662 can puncture an airtight film or membrane over an opening to the solution container 660 to form a fluid path between the bulk of the solution and an output of the nozzle 652 via the needle electrode 662.

Optionally, the consumable housing 658 may be replaceable within the housing 651 in favor of another consumable housing 658, for instance, when the former is empty of solution or has a detected amount of solution below a predetermined fill level. Additionally or alternatively, the entire output assembly 650 may be removed from the body assembly 610 and replaced with another output assembly, such as another output assembly 650.

The needle electrode 662 may be hollow, as eluded to above, and may be conductive. Thus, the needle electrode 662 may serve as both a fluid path for the solution and a conductive surface to allow charge created by an electric field caused by the high voltage HV to be injected into the solution. More specifically, the needle electrode 662, which may be part of the nozzle 652, may be hollow so as to receive solution from the solution container 660 and output the solution at or just before the nozzle tip 670. Generally, the flow path formed by the needle electrode and the nozzle tip 670 may be formed of materials that do not or do not substantially chemically or physio-chemically react with the solution in any substantial way.

Figure 5:
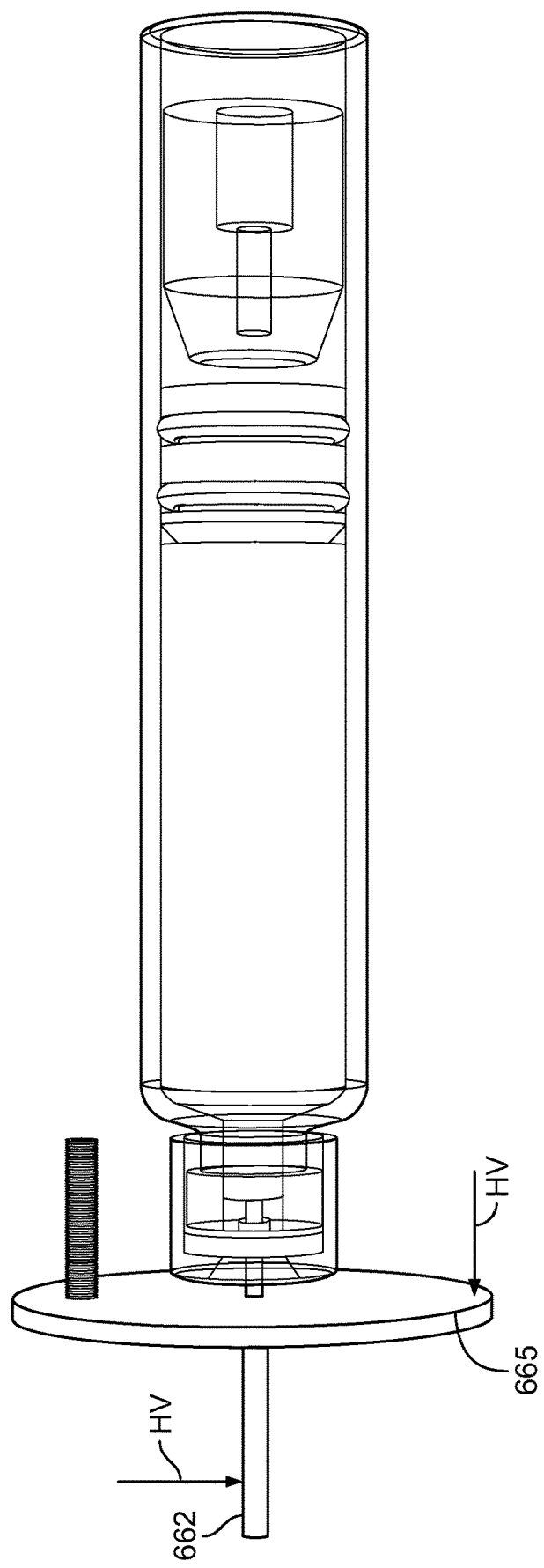
FIG. 5 is a diagrammatic representation of a portion of the consumable portion of FIG. 4, according to one or more embodiments of the disclosed subject matter.

Optionally, no resistor may be provided in the path of high voltage HV for the needle electrode 662, such as illustrated diagrammatically in FIG. 5. Optionally, the needle electrode 662 may be set back from the nozzle tip 670, such as shown in FIG. 4 and the right image of FIG. 7, by a setback amount SB. In one or more embodiments, the needle electrode 662 may be set back SB preferably about 1.5 mm to about 2.5 mm from the nozzle tip 670, more preferably about 2.5 mm, even more preferably about 1.5 mm. Such setback SB of the needle electrode 662 may reduce lateral dispersion of the electrospun solution, which may make the web of electrospun fibers more targeted.

Optionally, in one or more embodiments, such as the embodiment shown in FIGS. 2-7, a disc electrode 665 may be provided as part of the output assembly 650 or as part of the nozzle 652, if the nozzle 652 is identified as a component separate from the output assembly 650. Alternatively, in one or more embodiments, the disc electrode 665 may not be provided, and only the needle electrode 662 may be provided. Optionally, the high voltage HV paths to the needle electrode 662 and the disc electrode 665 may be distinct, as illustrated diagrammatically in FIG. 5. Optionally, no resistor may be provided in the path of high voltage HV for the disc electrode 665, such as illustrated diagrammatically in FIG. 5. Further, the disc electrode 665 may have the same polarity as the needle electrode 662. The electric field created by the disc electrode 665, which may be viewed as a separate electric field from the electric field of the needle electrode 662, may reduce lateral dispersion of the electrospun solution, which may make the web of electrospun fibers more targeted.

The nozzle 652 may be removable from the housing 651, for instance, via threaded connections, such as illustrated in FIG. 7. Thus, different nozzles may be implemented according to desired electrospin or electrospray characteristics. Further, the nozzle 652 may be comprised of an insulating material or materials with appropriate dielectric constant(s) to electrically insulate the needle electrode 662. For example, in one or more embodiments of the disclosed subject matter, a liner/sheath 671 may be provided for the needle electrode 662, where the liner/sheath 671 may run past the tip of the needle electrode 662 on one side and to the other end of the needle electrode 662 on the other side, for instance, to the disc electrode 665 (in a case where the disc electrode 665 is provided). Such linear/sheath 671 may be a polytetrafluoroethylene (PTFE) liner/sheath, for instance, and may prevent or minimize solution from sticking or clogging to the nozzle at a point where a Taylor cone is formed, for instance, in the case of electrospinning. Optionally, as illustrated in FIG. 7, a portion of the nozzle 652 may be formed of a first non-conductive material, for instance, PTFE, and a portion of the nozzle 652 removably coupleable to the housing 651 may be formed of a second non-conductive material, for instance, polypropylene (PP).

FIG. 8 is a basic flow chart of a method 800 according to one or more embodiments of the disclosed subject matter.

At 802, the method 800 can include providing a device or a system according to an embodiment of the disclosed subject matter. Optionally, the providing at 802 can include replacing the solution of the device or system. For example, an entire output assembly may be coupled to a body assembly according to embodiments described herein, such output assembly having a desired solution to output from the device or system. As another example, only a container (e.g., a carpule, cartridge, etc.) of the output assembly that contains the desired solution can be provided, for instance, replaced when empty or a change in type of solution is desired.

At 804, the method 800 can provide using the provided device or system, for instance, as set forth herein. Such using can include depositing the solution on a deposit surface, such as a user's skin. Optionally, the electrosprayed or electrospun solution may be deposited on top of a cosmetic already applied to the skin. Alternatively, the electrosprayed or electrospun solution may be deposited directly on the skin. Optionally, another layer (or layers), for instance, a cosmetic layer, may be provided on the solution deposited directly on the skin. Thus, in one or more embodiments, the deposited electrosprayed or electrospun solution may form part of a so-called multi-layer application, as either a base layer or a higher-level layer, such as a middle or outer layer.

At 806, the method 800 may include replacing the solution of the device or system, for instance, when the solution has been expended or simply when a change in type of solution is desired. As noted above, the entire output assembly may be replaced to change the solution or, alternatively, only a container (e.g., a carpule, cartridge, etc.) of the output assembly that contains the desired solution can be replaced to change the solution.

Embodiments of the disclosed subject matter may provide for an electrospinning or electrospraying process that may be functionally independent of orientation of a solution output device, particularly a portable, hand-held solution output device, and may be positioned to output solution on a deposit surface in relatively difficult areas, such as a particularly difficult area of a human's body. Also, embodiments of the disclosed subject matter can implement a modular construction, allowing multiple physical configurations, types of solution, and/or solution output characteristics. Additionally, embodiments of the disclosed subject matter can allow for solution to be readily replaced without contamination between samples.

Embodiments of the disclosed subject matter may also be as set forth according to the parentheticals in the following paragraphs.

(1) A portable, hand-held device for electrospinning or electrospraying toward a deposit surface a predetermined solution formulated for the device, the device comprising: a durable portion; and a consumable portion coupled to the durable portion, wherein the consumable portion includes: a hollow nozzle configured to output the solution from a nozzle tip thereof, the hollow nozzle having a hollow electrode that defines a first portion of a flow path of the solution to outside the device, and the nozzle tip defines a second portion of the flow path, and a housing configured to contain a predetermined maximum volume of the solution, and output the solution to the hollow electrode, wherein the durable portion includes: a drive mechanism configured to cause solution from the housing to be output to the hollow electrode, and a user control interface configured to receive manual input from a user to control the drive mechanism and application of a high voltage to the hollow electrode to create an electric field for application to the solution to electrospin or electrospray the solution from the hollow nozzle toward the deposit surface, and wherein circuitry is configured to provide the high voltage to the hollow electrode.

(2) The device according to (1), wherein a distal end of the hollow electrode is set back or recessed from the nozzle tip.

(3) The device according to (1) or (2), wherein the set back or amount of recess is about 1.5 mm to about 2.5 mm from the nozzle tip.

(4) The device according to any one of (1) to (3), wherein the solution is a polymer solution in the form of a water insoluble polymer having a coating formation ability.

(5) The device according to any one of (1) to (4), wherein the solution is a cosmetic formulation.

(6) The device according to any one of (1) to (5), wherein the high voltage is supplied to the hollow electrode either directly or indirectly.

(7) The device according to any one of (1) to (6), wherein the high voltage is supplied to the hollow electrode without going through a resistor.

(8) The device according to any one of (1) to (7), wherein the housing configured to contain the predetermined maximum volume of the solution includes a solution container that contains the predetermined maximum volume of the solution, the solution container being removable from the housing and replaceable with another solution container.

(9) The device according to any one of (1) to (8), further comprising a ground path route for grounding the user of the device.

(10) The device according to any one of (1) to (9), wherein the consumable portion further includes a secondary electrode configured to receive the high voltage from the circuitry.

(11) The device according to any one of (1) to (10), wherein the secondary electrode is in the form of a disc, a plate, or a flange.

(12) The device according to any one of (1) to (11), wherein the housing configured to contain the predetermined maximum volume of the solution is a carpule.

(13) The device according to any one of (1) to (12), wherein the durable portion includes a housing that houses the drive mechanism and that provides the user control interface, the durable portion being configured to be held by one hand of the user, the user control interface being operable by a finger or a thumb of the user when held by said one hand of the user.

(14) The device according to any one of (1) to (13), wherein the device is configured to receive the high voltage from a base station remote from the device, via a transmission medium.

(15) The device according to any one of (1) to (14), wherein the transmission medium is a flexible cable or cord comprised of a bundle of electrical transmission lines, including at least one high voltage electrical transmission line configured to transmit the high voltage from the base station to the device.

(16) The device according to any one of (1) to (15), further comprising a base station, the base station including a receptacle configured to receive and stow the device.

(17) The device according to any one of (1) to (16), wherein the user control interface is configured to operate the device in at least two operational states.

(18) The device according to any one of (1) to (17), wherein a first operational state is a dormant ("Off") state in which the drive mechanism is not energized, and the high voltage is not provided by or to the device, wherein a second operational state is a priming ("Prime") state in which the drive mechanism is active, and the high voltage is not provided by or to the device, and/or wherein a third operational state is an active ("Active") state in which the drive mechanism is active, and the high voltage is provided to the hollow electrode.

(19) The device according to any one of (1) to (18), wherein, in the third operational state, the drive mechanism urges the solution from the housing to the nozzle tip via the hollow electrode when the high voltage is provided to the hollow electrode, and the solution is electrospun at the nozzle tip of the hollow nozzle.

(20) The device according to any one of (1) to (19), wherein the consumable portion is removably coupled to the durable portion, the consumable portion being removable from the durable portion for replacement with another consumable portion.

(21) The device according to any one of (1) to (20), wherein the durable portion includes a first housing, and the consumable portion includes a second housing, different from the first housing, the second housing of the consumable portion being detachable and reattachable to the first housing of the durable portion.

(22) The device according to any one of (1) to (21), wherein the user control interface includes one of a trigger, a tactile switch, and a tactile button.

(23) The device according to any one of (1) to (22), wherein the trigger, the tactile switch, or the tactile button are configured to operate the device according to multiple operational states, excluding a non-operational state.

(24) The device according to any one of (1) to (23), wherein the durable portion includes a high voltage power supply configured to output the high voltage.

(25) The device according to any one of (1) to (24), wherein the durable portion includes a low voltage power supply.

(26) The device according to any one of (1) to (25), wherein the consumable portion includes a housing and the hollow nozzle, the hollow nozzle being removably coupled to the housing such that the hollow nozzle is removable from the housing.

(27) The device according to any one of (1) to (26), further comprising an insulating sheath around a portion of the hollow electrode, including a distal end of the hollow electrode.

(28) The device according to any one of (1) to (27), wherein the circuitry is configured to implement presets for one or more operational parameters of the device, the one or more operational parameters including: the high voltage, an operating current corresponding to the high voltage, a drive speed of the drive mechanism, and a drive direction of the drive mechanism.

(29) The device according to any one of (1) to (28), wherein the drive mechanism is or includes a linear actuator.

(30) The device according to any one of (1) to (29), wherein the drive mechanism is or includes a stepper motor.

(31) The device according to any one of (1) to (30), wherein the drive mechanism is or includes a positive displacement mechanism.

(32) The device according to any one of (1) to (31), wherein the consumable portion further includes a secondary electrode configured to receive the high voltage, the secondary electrode surrounding a portion of the hollow electrode.

(33) The device according to any one of (1) to (32), wherein the secondary electrode is in the form of a disc, a plate, or a flange.

(34) The device according to any one of (1) to (33), wherein control of the drive mechanism and a voltage amount of the high voltage causes variation of one or more of a volume of electrospun fibers output by device, dispersion of electrospun fibers output by the device, and size of electrospun fibers output by the device.

(35) The device according to any one of (1) to (34), wherein the circuitry is configured to detect a distance state of the device based on signals from a position sensor configured to sensor position of the nozzle tip relative to the deposit surface, and one or more of disable the drive mechanism and supply of the high voltage to the hollow electrode, enable or reenable the drive mechanism and supply of the high voltage to the hollow electrode, and activate at least one indication to the user representative of the detected distance state.

(36) the device according to any one of (1) to (35), wherein the circuitry is configured to detect a distance state of the device based on signals from a position sensor configured to sensor position of the nozzle tip relative to the deposit surface, and output one or more indicators to the user based on sensed or detected characteristics of the device.

(37) The device according to any one of (1) to (36), wherein the at least indicator includes a light visible to the user that is specific to the detected distance state.

(38) The device according to any one of (1) to (37), wherein the circuitry is configured to switch between an operative state and an inoperative state of the device based on sensed distance of the nozzle tip to the deposit surface.

(39) The device according to any one of (1) to (38), wherein the circuitry includes a fill level detector configured to detect an amount of solution in the housing.

(40) The device according to any one of (1) to (39), wherein the circuitry is configured to output a visual indication corresponding to the detected amount of solution in the housing.

(41) The device according to any one of (1) to (40), wherein the circuitry includes a haptic feedback mechanism configured to provide feedback to the user when the user is holding the durable portion.

(42) The device according to any one of (1) to (41), wherein the haptic feedback is at least one of vibration and tapping.

(43) The device according to any one of (1) to (42), wherein the solution is a polymer solution in the form of a water insoluble polymer having a coating formation ability.

(44) The device according to any one of (1) to (43), wherein the water insoluble polymer having the coating formation ability is selected from the group: completely saponified polyvinyl alcohol, insolubilized after the formation of a coating; partially saponified polyvinyl alcohol, cross-linked after the formation of a coating when used in combination with a cross-linking agent; a oxazoline modified silicone, including a poly(N-propanoylethyleneimine)-grafted dimethylsiloxane/γ-aminopropylmethylsiloxane copolymer; polyvinylacetal diethylamino acetate; zein (main component of corn proteins); polyester; polylactic acid (PLA); an acrylic resin, including a polyacrylonitrile resin or a polymethacrylic acid resin; a polystyrene resin; a polyvinyl butyral resin; a polyethylene terephthalate resin; a polybutylene terephthalate resin; a polyurethane resin; a polyamide resin; a polyimide resin; a polyamideimide resin; and polyvinyl butyral resin.

(45) The device according to any one of (1) to (44), wherein the solution is a liquid agent comprising a component (a), a component (b), and a component (c) as follows: component (a) is one or more volatile substances selected from the group consisting of alcohols and ketones; component (b) is water; and component (c) is one or more polymers having a coating formation ability.

(46) The device according to any one of (1) to (45), wherein the alcohols include one or more of chain aliphatic monohydric alcohols, one or more cyclic aliphatic monohydric alcohols, and/or one or more aromatic monohydric alcohols, and wherein the ketones include one or more of acetone, methyl ethyl ketone, and methyl isobutyl ketone.

(47) The device according to any one of (1) to (46), wherein the alcohols consist of at least one member selected from ethanol, isopropyl alcohol, and butyl alcohol.

(48) The device according to any one of (1) to (47), wherein the alcohols consist of at least one member selected from ethanol and butyl alcohol.

(49) The device according to any one of (1) to (48), wherein the alcohols consist of ethanol.

(50) A portable, hand-held device for electrospinning toward a deposit surface a predetermined solution formulated for the device, the device comprising: a durable portion; and a consumable portion coupled to the durable portion, wherein the consumable portion includes: a hollow nozzle configured to output the solution from a nozzle tip thereof, the hollow nozzle having a hollow electrode that defines a first portion of a flow path of the solution to outside the device, and the nozzle tip defines a second portion of the flow path, the hollow electrode being configured to output received high voltage supplied via a first conduction path, another electrode configured to output a received high voltage supplied via a second conduction path different from the first conduction path, and a housing configured to contain a predetermined maximum volume of the solution, and output the solution to the hollow electrode, wherein the durable portion includes: a drive mechanism configured to cause solution from the housing to be output to the hollow electrode, and a user control interface configured to receive manual input from a user to control the drive mechanism and application of the high voltage to the hollow electrode and the high voltage to the another electrode to create an electric field for application to the solution to electrospin the solution from the hollow nozzle toward the deposit surface, and wherein circuitry is configured to provide the high voltage to the hollow electrode and the another electrode.

(51) The device according to (50), wherein said another electrode is one of a conductive disc, a conductive plate, or a conductive flange

(52) The device according to (50) or (51), wherein said another electrode and said hollow electrode are coaxially arranged, said another electrode having a channel through which the hollow electrode passes.

(53) The device according to any one of (50) to (52), wherein said another electrode and said hollow electrode are electrically connected to each other.

(54) The device according to any one of (50) to (53), wherein the high voltage supplied to said another electrode is different from the high voltage supplied to said hollow electrode.

(55) The device according to any one of (50) to (54), wherein said another electrode and said hollow electrode are electrically insulated or isolated from each other.

(56) The device according to any one of (50) to (55), wherein a distal end of the hollow electrode is set back or recessed from the nozzle tip.

(57) The device according to any one of (50) to (56), wherein the set back or amount of recess is about 2.5 mm from the nozzle tip.

(58) The device according to any one of (50) to (57), wherein the solution is a cosmetic formulation.

(59) The device according to any one of (50) to (58), wherein the high voltage is supplied to the hollow electrode and said another electrode either directly or indirectly.

(60) The device according to any one of (50) to (59), wherein the high voltage is supplied to the hollow electrode without going through a resistor in the consumable portion, and wherein the high voltage is supplied to said another electrode without going through a resistor in the consumable portion.

(61) The device according to any one of (50) to (60), wherein said another electrode is arranged between a distal end of the hollow electrode and the housing.

(62) The device according to any one of (50) to (61), wherein said another electrode and the hollow electrode are configured to operate at a same polarity.

(63) The device according to any one of (50) to (62), wherein said another electrode and the hollow electrode are configured to receive the high voltage at a same time to generate at the same time respective electric fields or electric field portions.

(64) The device according to any one of (50) to (63), wherein said another electrode is configured to apply a potential gradient to the solution at the hollow nozzle.

(65) The device according to any one of (50) to (64), wherein the solution is a polymer solution.

(66) The device according to any one of (50) to (65), wherein the polymer solution in the form of a water insoluble polymer having a coating formation ability.

(67) The device according to any one of (50) to (66), wherein the water insoluble polymer having the coating formation ability is selected from the group: completely saponified polyvinyl alcohol, insolubilized after the formation of a coating; partially saponified polyvinyl alcohol, cross-linked after the formation of a coating when used in combination with a cross-linking agent; a oxazoline modified silicone, including a poly(N-propanoylethyleneimine)-grafted dimethylsiloxane/γ-aminopropylmethylsiloxane copolymer; polyvinylacetal diethylamino acetate; zein (main component of corn proteins); polyester; polylactic acid (PLA); an acrylic resin, including a polyacrylonitrile resin or a polymethacrylic acid resin; a polystyrene resin; a polyvinyl butyral resin; a polyethylene terephthalate resin; a polybutylene terephthalate resin; a polyurethane resin; a polyamide resin; a polyimide resin; a polyamideimide resin; and polyvinyl butyral resin.

(68) The device according to any one of (50) to (67), wherein the solution is a liquid agent comprising a component (a), a component (b), and a component (c) as follows: component (a) is one or more volatile substances selected from the group consisting of alcohols and ketones; component (b) is water; and component (c) is one or more polymers having a coating formation ability.

(69) The device according to any one of (50) to (68), wherein the alcohols include one or more of chain aliphatic monohydric alcohols, one or more cyclic aliphatic monohydric alcohols, and/or one or more aromatic monohydric alcohols, and wherein the ketones include one or more of acetone, methyl ethyl ketone, and methyl isobutyl ketone.

(70) The device according to any one of (50) to (69), wherein the alcohols consist of at least one member selected from ethanol, isopropyl alcohol, and butyl alcohol.

(71) The device according to any one of (50) to (70), wherein the alcohols consist of at least one member selected from ethanol and butyl alcohol.

(72) The device according to any one of (50) to (71), wherein the alcohols consist of ethanol.

(73) An electrospinning or electrospraying system comprising: means for providing high voltage; means for generating an electric field and applying the electric field to solution based on the high voltage; means for outputting the solution to receive application of the electric field; means for outputting the solution as electrospun or electrosprayed solution; and means for controlling the means for generating the electric field and the means for outputting the solution as the electrospun or electrosprayed solution.

(74) A method of providing, making, or using a device or a system according to any one of (1) to (73).

(75) The method according to (74), wherein the method comprises providing the device according to any one of (1) to (72) or the system according to (73); and using the device or the system.

(76) The method according to (74) or (75), wherein the deposit surface is skin.

(77) The method according to any one of (74) to (76), wherein said using the device or system includes electrospraying or electrospinning the solution on top of a cosmetic already applied to the skin.

(78) The method according to any one of (74) to (77), wherein said using the device or system includes electrospraying or electrospinning the solution directly on the skin, followed by providing a cosmetic directly or indirectly on the solution.

(79) The method according to any one of (74) to (78), wherein said providing includes replacing the solution prior to said using the device or system.

(80) The method according to any one of (74) to (79), further comprising replacing the solution after said using the device or system.

(81) A portable, hand-held device for electrospinning or electrospraying toward a deposit surface a predetermined solution formulated for the device, the device comprising: a durable portion having a first end and a second end opposite the first end; and a consumable portion coupled to the first end of the durable portion, wherein the consumable portion includes: an electrode, a hollow nozzle configured to output the solution from a nozzle tip thereof, the hollow nozzle defining a first portion of a flow path of the solution to outside the device, and the nozzle tip defines a second portion of the flow path, and a housing configured to contain a predetermined maximum volume of the solution, and output the solution to the hollow nozzle, wherein the durable portion includes: a drive mechanism configured to cause solution from the housing to be output to the hollow nozzle, and a user control interface including a switch configured to receive manual input from a user in the form of a pressing operation and move radially inward to control the drive mechanism and application of a high voltage to the electrode to create an electric field for application to the solution to electrospin or electrospray the solution from the hollow nozzle toward the deposit surface, wherein circuitry is configured to provide the high voltage to the hollow electrode, and wherein the switch is closer to the second end of the durable portion than the housing of the consumable portion is to the second end of the durable portion.

(82) The device according to (81), wherein a distal end of the electrode is inside the hollow nozzle that defines the first portion of the flow path and is set back or recessed from the nozzle tip.

(83) The device according to (81) or (82), wherein the solution is a polymer solution in the form of a water insoluble polymer having coating and fiber formation ability.

(84) The device according to any one of (81) to (83), wherein the housing configured to contain the predetermined maximum volume of the solution includes a solution container that contains the predetermined maximum volume of the solution, the solution container being removable from the housing and replaceable with another solution container.

(85) The device according to any one of (81) to (84), wherein the durable portion includes a housing that houses the drive mechanism and that provides the user control interface, the durable portion being configured to be held by one hand of the user, the user control interface being operable by a finger or a thumb of the user to depress and release the switch when held by said one hand of the user.

(86) The device according to any one of (81) to (85), wherein the device is configured to receive the high voltage from a base station remote from the device, via a transmission medium.

(87) The device according to any one of (81) to (86), wherein the housing of the consumable portion is detachable and reattachable to a housing of the durable portion.

(88) The device according to any one of (81) to (87), wherein the hollow nozzle is removably coupled to the housing such that the hollow nozzle is removable from the housing.

(89) The device according to any one of (81) to (88), further comprising an insulating sheath around a portion of the electrode, including a distal end of the electrode, wherein the electrode is hollow.

(90) The device according to any one of (81) to (89), wherein the circuitry is configured to implement presets for one or more operational parameters of the device, the one or more operational parameters including: the high voltage, an operating current corresponding to the high voltage, a drive speed of the drive mechanism, and a drive direction of the drive mechanism.

(91) The device according to any one of (81) to (90), wherein the solution is a liquid agent comprising a component (a), a component (b), and a component (c) as follows: component (a) is one or more volatile substances selected from the group consisting of alcohols and ketones; component (b) is water; and component (c) is one or more polymers having a coating formation ability.

(92) The device according to any one of (81) to (91), wherein the device is configured to output the electrospun or electrosprayed solution from the hollow nozzle at a flow rate of from about 0.05 to about 0.5 ml/min using about 6 kV to about 30 kV as the high voltage, and wherein the solution contains greater than 70% alcohol.

(93) A portable, hand-held device for electrospinning or electrospraying toward a deposit surface a predetermined solution formulated for the device, the device comprising: a durable portion; a consumable portion coupled to the durable portion; and a conducting rod arranged along an axial direction of the device, wherein the consumable portion includes: an electrode, a hollow nozzle configured to output the solution from a nozzle tip thereof, the hollow nozzle defining a first portion of a flow path of the solution to outside the device, and the nozzle tip defines a second portion of the flow path, and a housing configured to contain a predetermined maximum volume of the solution, and output the solution to the hollow nozzle, wherein the durable portion includes: a drive mechanism configured to cause solution from the housing to be output to the hollow nozzle, and a user control interface configured to receive manual input from a user to control the drive mechanism and application of a high voltage to the hollow electrode to create an electric field for application to the solution to electrospin or electrospray the solution from the hollow nozzle toward the deposit surface, and wherein circuitry is configured to provide the high voltage to the hollow electrode, wherein the conducting rod is arranged radially outward of the housing of the consumable portion configured to contain the solution.

(94) The device according to (93), wherein the solution is a liquid agent comprising a component (a), a component (b), and a component (c) as follows: component (a) is one or more volatile substances selected from the group consisting of alcohols and ketones; component (b) is water; and component (c) is one or more polymers having a coating formation ability, wherein the alcohols include one or more of chain aliphatic monohydric alcohols, one or more cyclic aliphatic monohydric alcohols, and/or one or more aromatic monohydric alcohols, and wherein the ketones include one or more of acetone, methyl ethyl ketone, and methyl isobutyl ketone.

(95) The device according to (93) or (94), wherein a first end of the conducting rod is arranged to receive the high voltage from a power supply, and a second end of the conducting rod opposite the first end is electrically connected to the electrode using a resilient member.

(96) A portable, hand-held device for electrospinning or electrospraying toward a deposit surface a predetermined solution formulated for the device, the device comprising: a durable portion having a first end and a second end opposite the first end; and a consumable portion having a third end and a fourth end opposite the third end, the consumable portion being removably coupled to the durable portion, wherein the consumable portion includes: an electrode, a hollow nozzle configured to output the solution from a nozzle tip thereof, the hollow nozzle defining a first portion of a flow path of the solution to outside the device, and the nozzle tip defines a second portion of the flow path, and a housing configured to contain a predetermined maximum volume of the solution, and output the solution to the hollow nozzle, wherein the durable portion includes: a drive mechanism configured to cause solution from the housing to be output to the hollow nozzle, and a user control interface configured to receive manual input from a user to control the drive mechanism and application of a high voltage to the hollow electrode to create an electric field for application to the solution to electrospin or electrospray the solution from the hollow nozzle toward the deposit surface, wherein circuitry is configured to provide the high voltage to the hollow electrode, wherein the third end of the consumable portion is removably coupled to the first end of the durable portion at an interface such that outer surfaces of the consumable portion and outer surfaces of the durable portion are congruent at the interface and such that the consumable portion and the durable portion are aligned on a central longitudinal axis at a radial center of the device, and wherein a portion of the consumable portion extends from the first end of the durable portion more a portion of the consumable portion inside the durable portion.

(97) The device according to (96), wherein the consumable portion and the durable portion, when the consumable portion is removably coupled to the durable portion, are in the form of a stylus.

(98) The device according to (96) or (97), wherein a ratio of an axial width to an orthogonal width of the durable portion at a region of the user control interface to receive the manual input from the user is about 3.5:1 to about 12:1.

(99) The device according to any one of (96) to (98), further comprising a conducting rod arranged along an axial direction of the device, wherein the conducting rod is arranged radially outward of the housing of the consumable portion configured to contain the solution.

(100) The device according to any one of (96) to (99), wherein the user control interface includes a switch configured to receive the manual input from the user in the form of a pressing operation and move radially inward to control the drive mechanism and application of the high voltage to the electrode to create the electric field for application to the solution to electrospin or electrospray the solution from the hollow nozzle toward the deposit surface, and wherein the switch is closer to the second end of the durable portion than the housing of the consumable portion is to the second end of the durable portion.

(101) A method comprising providing the device according to any one of (81) to (100); and using the provided device.

(102) The method according to (101), wherein the deposit surface is skin.

(103) The method according to (101) or (102), wherein said using the device includes electrospraying or electrospinning the solution on top of a cosmetic already applied to the skin.

(104) The method according to any one of (101) to (103), wherein said using the device includes electrospraying or electrospinning the solution directly on the skin, followed by providing a cosmetic directly or indirectly on the solution.

(105) The method according to any one of (101) to (104), wherein said providing includes replacing the solution prior to said using the device.

(106) The method according to any one of (101) to (105), further comprising replacing the solution after said using the device.

Having now described embodiments of the disclosed subject matter, it should be apparent to those skilled in the art that the foregoing is merely illustrative and not limiting, having been presented by way of example only. Thus, although particular configurations have been discussed and illustrated herein, other configurations can be and are also employed. Further, numerous modifications and other embodiments (e.g., combinations, rearrangements, etc.) are enabled by the present disclosure and are contemplated as falling within the scope of the disclosed subject matter and any equivalents thereto. Features of the disclosed embodiments can be combined, rearranged, omitted, etc., within the scope of described subject matter to produce additional embodiments. Furthermore, certain features may sometimes be used to advantage without a corresponding use of other features. Accordingly, Applicant intends to embrace all such alternatives, modifications, equivalents, and variations that are within the spirit and scope of the present disclosure.

List of Elements 100 system
200 base station
202 control panel
204 controller
206 power source
208 handset receptacle
300 handset
310 body assembly/durable
350 output assembly/consumable
352 nozzle
HV high voltage
400 transmission medium
500 grounding line
501 grounding strap
502 grounding line
600 handset
610 body assembly
611 housing
612 user control interface
614 motor
616 actuator
618 circuitry
620 distance sensor
622 fill level detector
624 HV connector
626 consumable detector
627 pin
628 light source
630 haptic feedback mechanism
633 pressing member
635 pressed member
650 output assembly
651 housing
652 nozzle
653 light path
654 conducting rod
655 connector
656 high voltage connector
657 feedback indicator
658 consumable housing
659 bung
660 solution container
662 needle electrode
SB set back
665 disc electrode
670 nozzle tip
671 liner/sheath
800 method
802 step
804 step
806 step

The invention claimed is:

1. A portable, hand-held device for electrospinning or electrospraying toward a deposit surface a predetermined solution formulated for the device, the device comprising:
   a durable portion having a first end and a second end opposite the first end; and
   a consumable portion coupled to the first end of the durable portion,
   wherein the consumable portion includes:

an electrode,
a hollow nozzle configured to output the solution from a nozzle tip thereof, the hollow nozzle defining a first portion of a flow path of the solution to outside the device, and the nozzle tip defines a second portion of the flow path, and
a housing configured to contain a predetermined maximum volume of the solution, and output the solution to the hollow nozzle,
wherein the durable portion includes:
a drive mechanism configured to cause solution from the housing to be output to the hollow nozzle, and
a user control interface including a switch configured to receive manual input from a user in the form of a pressing operation and move radially inward to control the drive mechanism and application of a high voltage to the electrode to create an electric field for application to the solution to electrospin or electrospray the solution from the hollow nozzle toward the deposit surface,
wherein circuitry is configured to provide the high voltage to the electrode,
wherein the switch is closer to the second end of the durable portion than the housing of the consumable portion is to the second end of the durable portion, and
wherein no portion of the switch overlaps the consumable portion in a top plan view of the device.

2. The device according to claim 1, wherein a distal end of the electrode is inside the hollow nozzle that defines the first portion of the flow path and is set back or recessed from the nozzle tip.

3. The device according to claim 1, wherein the solution is a polymer solution in the form of a water insoluble polymer having coating and fiber formation ability.

4. The device according to claim 1, wherein the housing configured to contain the predetermined maximum volume of the solution includes a solution container that contains the predetermined maximum volume of the solution, the solution container being removable from the housing and replaceable with another solution container.

5. The device according to claim 1, wherein the durable portion includes a housing that houses the drive mechanism and that provides the user control interface, the durable portion being configured to be held by one hand of the user, the user control interface being operable by a finger or a thumb of the user to depress and release the switch when held by said one hand of the user.

6. The device according to claim 1, wherein the device is configured to receive the high voltage from a base station remote from the device, via a transmission medium.

7. The device according to claim 1, wherein the housing of the consumable portion is detachable and reattachable to a housing of the durable portion.

8. The device according to claim 1, wherein the hollow nozzle is removably coupled to the housing such that the hollow nozzle is removable from the housing.

9. The device according to claim 1, further comprising an insulating sheath around a portion of the electrode, including a distal end of the electrode, wherein the electrode is hollow.

10. The device according to claim 1, wherein the circuitry is configured to implement presets for one or more operational parameters of the device, the one or more operational parameters including: the high voltage, an operating current corresponding to the high voltage, a drive speed of the drive mechanism, and a drive direction of the drive mechanism.

11. The device according to claim 1, wherein the solution is a liquid agent comprising a component (a), a component (b), and a component (c) as follows: component (a) is one or more volatile substances selected from the group consisting of alcohols and ketones; component (b) is water; and component (c) is one or more polymers having a coating formation ability.

12. The device according to claim 1,
wherein the device is configured to output the electraspun or electrosprayed solution from the hollow nozzle at a flow rate of from about 0.05 to about 0.5 ml/min using about 6 kV to about 30 kV as the high voltage, and
wherein the solution contains greater than 70% alcohol.

13. The device according to claim 1, wherein a minimum distance from the switch to the second end of the durable portion is less than a minimum distance from the housing of the consumable portion to the second end of the durable portion.

14. The device according to claim 1,
wherein the housing of the consumable portion that contains the predetermined maximum volume of the solution has a proximal end at which the solution is output and a distal end opposite the proximal end, and
wherein the distal end of the housing is closer to the nozzle tip than the switch is to the nozzle tip.

15. The device according to claim 1,
wherein the housing of the consumable portion that contains the predetermined maximum volume of the solution has a proximal end at which the solution is output and a distal end opposite the proximal end, and
wherein no portion of the first end of the durable portion extends past the proximal end of the housing.

16. The device according to claim 1, wherein the electrode is hollow.

17. The device according to claim 1, wherein removal of the pressing operation to the switch ceases output of the solution from the hollow nozzle.

18. A portable, hand-held device for electrospinning or electrospraying toward a deposit surface a predetermined solution formulated for the device, the device comprising:
a durable portion having a first end and a second end opposite the first end; and
a consumable portion coupled to the first end of the durable portion,
wherein the consumable portion includes:
an electrode,
a hollow nozzle configured to output the solution from a nozzle tip thereof, the hollow nozzle defining a first portion of a flow path of the solution to outside the device, and the nozzle tip defines a second portion of the flow path, and
a housing configured to contain a predetermined :maximum volume of the solution, and output the solution to the hollow nozzle,
wherein the durable portion includes:
a drive mechanism configured to cause solution from the housing to be output to the hollow nozzle, and
a user control interface including a switch configured to receive manual input from a user in the form of a pressing operation and move radially inward to control the drive mechanism and application of a high voltage to the electrode to create an electric field for application to the solution to electrospin o electrospray the solution from the hollow nozzle toward the deposit surface,
wherein circuitry is configured to provide the high voltage to the electrode, wherein the switch is closer to the second end of the durable portion than the housing of the consumable portion is to the second end of the durable portion, wherein the housing of the consumable portion that contains the predetermuied maximum volume of the solution has a proximal end at which the solution is output and a distal end opposite the proximal end, and wherein the distal end of the housing is closer to the nozzle tip than the switch is to the nozzle tip.

19. A method comprising:

providing a portable, hand-held device for electrospinning or electrospraying toward a deposit surface a predetermined solution formulated for the device; and using the device to electrospin or electrospray the predetermined solution toward the deposit surface, the device comprising:

a durable portion having a first end and a second end opposite the first end; and a consumable portion coupled to the first end of the durable portion, wherein the consumable portion includes:

an electrode, a hollow nozzle configured to output the solution from a nozzle tip thereof the hollow nozzle defining a first portion of a flow path of the solution to outside the device, and the nozzle tip defines a second portion of the flow path, and a housing configured to contain a predetermined maximum volume of the solution, and output the solution to the hollow nozzle, wherein the durable portion includes:

a drive mechanism configured to cause solution from the housing to be output to the hollow nozzle, and a user control interface including a switch configured to receive manual input from a user in the form of a pressing operation and move radially inward to control the drive mechanism and application of a high voltage to the electrode to create an electric field for application to the solution to electrospin or electrospray the solution from the hollow nozzle toward the deposit surface, wherein circuitry is configured to provide the high voltage to the electrode, wherein the switch is closer to the second end of the durable portion than the housing of the consumable portion is to the second end of the durable portion, and wherein no portion of the switch overlaps the consumable portion in a top plan view of the device.

* * * * *